(12) United States Patent
Lim et al.

(10) Patent No.: US 11,103,408 B2
(45) Date of Patent: Aug. 31, 2021

(54) OBSTETRIC AND GYNECOLOGIC DIAGNOSIS APPARATUS AND OBSTETRIC AND GYNECOLOGIC DIAGNOSIS METHOD USING THE SAME

(71) Applicant: SAMSUNG MEDISON CO., LTD., Hongcheon-gun (KR)

(72) Inventors: Sung-won Lim, Hongcheon-gun (KR); Ui Kim, Hongcheon-gun (KR); Jun-pil Moon, Hongcheon-gun (KR); Cheon-seop Shin, Hongcheon-gun (KR); Kil-su Ha, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 989 days.

(21) Appl. No.: 15/702,167

(22) Filed: Sep. 12, 2017

(65) Prior Publication Data

US 2018/0085271 A1    Mar. 29, 2018

Related U.S. Application Data

(60) Provisional application No. 62/398,689, filed on Sep. 23, 2016.

(30) Foreign Application Priority Data

Jul. 25, 2017 (KR) .......................... 10-2017-0094320

(51) Int. Cl.
*A61B 8/00* (2006.01)
*A61G 15/02* (2006.01)
(Continued)

(52) U.S. Cl.
CPC .......... *A61G 15/005* (2013.01); *A61B 5/4306* (2013.01); *A61B 5/70* (2013.01);
(Continued)

(58) Field of Classification Search
CPC combination set(s) only.
See application file for complete search history.

(56) References Cited

U.S. PATENT DOCUMENTS 4,168,099 A * 9/1979 Jacobs ................ A61G 15/005
297/325
4,938,464 A * 7/1990 Akiko ................ A61G 15/005
5/602
(Continued)

FOREIGN PATENT DOCUMENTS

CN        201572283 U       9/2010
CN        102711626 B       12/2014
(Continued)

OTHER PUBLICATIONS

Communication dated Jun. 4, 2019 issued by the European Intellectual Property Office in counterpart European Application No. 17853365.9.
(Continued)

*Primary Examiner* — Patricia J Park
(74) *Attorney, Agent, or Firm* — Sughrue Mion, PLLC

(57) ABSTRACT

Provided are an obstetric and gynecologic diagnosis apparatus and an obstetric and gynecologic diagnosis method using the same. The obstetric and gynecologic diagnosis apparatus includes a chair unit on which an object is mounted, the chair unit including an upper body support, a seat, and a leg cradle sequentially arranged in one direction and connected to each other; a storage configured to store body information of the object; an input interface configured to input identification (ID) information of the object; a controller configured to generate a control signal for moving at least one of the upper body support, the seat, and the leg cradle according to first body information of the object identified by the input ID information; and a driver configured
(Continued)

ured to generate a driving force for moving at least one of the upper body support, the seat, and the leg cradle according to the control signal.

20 Claims, 21 Drawing Sheets

(51) Int. Cl.
    *A61G 15/00*     (2006.01)
    *A61B 5/00*     (2006.01)
    *A61G 15/12*     (2006.01)
    *A61B 8/08*     (2006.01)
    *A61B 8/14*     (2006.01)
    *A61G 5/12*     (2006.01)
    *A61B 5/01*     (2006.01)
    *A61B 5/103*     (2006.01)

(52) U.S. Cl.
    CPC ................ *A61B 8/08* (2013.01); *A61B 8/14* (2013.01); *A61B 8/40* (2013.01); *A61B 8/4209* (2013.01); *A61B 8/461* (2013.01); *A61G 15/02* (2013.01); *A61G 15/12* (2013.01); *A61B 5/01* (2013.01); *A61B 5/103* (2013.01); *A61B 8/0866* (2013.01); *A61G 5/128* (2016.11)

(56) References Cited

U.S. PATENT DOCUMENTS

| | | | |
|---|---|---|---|
| 6,063,035 | A | 5/2000 | Sakamoto et al. |
| 6,629,927 | B1 | 10/2003 | Mesaros et al. |
| 6,716,167 | B1 * | 4/2004 | Henderson ........... A61G 15/005 600/407 |
| 8,376,103 | B1 | 2/2013 | Sliger |
| 8,449,455 | B2 | 5/2013 | Honda et al. |
| 8,496,380 | B2 | 7/2013 | Hornig |
| 9,072,489 | B2 | 7/2015 | Chono et al. |
| 9,235,973 | B2 | 1/2016 | Popescu |
| 9,492,341 | B2 | 11/2016 | Huster et al. |
| 9,610,197 | B2 | 4/2017 | Wellhöfer |
| 2010/0212087 | A1 * | 8/2010 | Leib ...................... G16H 40/20 5/81.1 R |
| 2011/0104634 | A1 | 5/2011 | Kyöstilä |
| 2012/0089419 | A1 | 4/2012 | Huster et al. |
| 2013/0165796 | A1 | 6/2013 | Tashiro |
| 2014/0039351 | A1 | 2/2014 | Mix et al. |
| 2014/0107487 | A1 | 4/2014 | Kim et al. |
| 2014/0128739 | A1 * | 5/2014 | Sundaran ................. A61B 8/54 600/459 |
| 2014/0243671 | A1 * | 8/2014 | Holl ..................... A61B 8/4209 600/443 |

FOREIGN PATENT DOCUMENTS

| | | |
|---|---|---|
| CN | 204016719 U | 12/2014 |
| EP | 1292259 B1 | 8/2013 |
| JP | 08000684 A | 1/1996 |
| JP | 2009291281 A | 12/2009 |
| JP | 201136589 A | 2/2011 |
| JP | 201172418 A | 4/2011 |
| JP | 2011182978 A | 9/2011 |
| JP | 201295934 A | 5/2012 |
| JP | 20144364 A | 1/2014 |
| JP | 2014515628 A | 7/2014 |
| KR | 1020050119921 A | 12/2005 |
| KR | 101268793 B1 | 5/2013 |
| KR | 1020140046754 A | 4/2014 |
| KR | 1020150052673 A | 5/2015 |
| KR | 101660833 B1 | 9/2016 |
| WO | 2005/120331 A1 | 12/2005 |
| WO | 2010150697 A1 | 12/2010 |
| WO | 2013112107 A1 | 8/2013 |
| WO | 2014198336 A1 | 12/2014 |

OTHER PUBLICATIONS

International Search Report and Written Opinion (PCT/ISA/210 and PCT/ISA/237), dated Dec. 22, 2017 by International Searching Authority in International Application No. PCT/KR2017/010147.
International Search Report and Written Opinion (PCT/ISA/210 and PCT/ISA/237), dated Dec. 20, 2017 by International Searching Authority in International Application No. PCT/KR2017/009966.
Communication dated May 4, 2020 issued by the European Intellectual Property Office in counterpart European Application No. 17853339.4.
Communication dated Jun. 18, 2021, from The China National Intellectual Property Administration in Application No. 201780059150. 1.

* cited by examiner

OBSTETRIC AND GYNECOLOGIC DIAGNOSIS APPARATUS AND OBSTETRIC AND GYNECOLOGIC DIAGNOSIS METHOD USING THE SAME

CROSS-REFERENCE TO RELATED APPLICATION

This application claims the benefit of U.S. Provisional Patent Application No. 62/398,689, filed on Sep. 23, 2016, in the U.S. Patent and Trademark Office, and the benefit of Korean Patent Application No. 10-2017-0094320, filed on Jul. 25, 2017, in the Korean Intellectual Property Office, the disclosures of which are incorporated herein in their entirety by reference.

BACKGROUND

1. Field

The present disclosure relates to an obstetric and gynecologic diagnosis apparatus including an ultrasound probe for providing an ultrasound image and an obstetric and gynecologic chair part, and an obstetric and gynecologic diagnosis method using the obstetric and gynecologic diagnosis apparatus.

2. Description of the Related Art

Ultrasound diagnosis apparatuses transmit an ultrasound signal generated by a transducer of a probe to an object and receive information regarding a signal reflected from the object, thereby obtaining an image of a part (e.g., a soft tissue or a blood stream) inside the object by using a noninvasive method.

Ultrasound diagnosis apparatuses are small and inexpensive, display images in real time, and are safe with respect to a fetus due to the lack of radioactive exposure, compared to other image diagnosis apparatuses, such as X-ray diagnosis apparatuses, computerized tomography (CT) scanners, magnetic resonance imaging (MRI) apparatuses, and nuclear medical diagnosis apparatuses. Therefore, ultrasound diagnosis apparatuses are widely used for obstetric and gynecologic diagnosis.

In the case of a mother who is carrying a fetus, her external appearance rapidly changes according to the growth of the fetus, and diagnostic items also change according to the growth of the fetus. According to the changes in the external appearance of the mother and diagnostic items, the diagnostic posture of the mother changes, and accordingly, the shape of a chair for obstetric and gynecologic diagnosis, on which the mother is seated to receive an obstetric or gynecologic diagnosis, should be changed.

SUMMARY

Provided is an obstetric and gynecologic diagnosis apparatus including a chair part for obstetric and gynecologic diagnosis of which a shape automatically changes according to body information and obstetric and gynecologic information of a mother who is carrying a fetus.

Provided is an obstetric and gynecologic diagnosis method of diagnosing body information of a mother and a fetus by using the obstetric and gynecologic diagnosis apparatus.

Additional aspects will be set forth in part in the description which follows and, in part, will be apparent from the description, or may be learned by practice of the presented embodiments.

According to an aspect of an embodiment, an obstetric and gynecologic diagnosis apparatus includes a chair unit on which an object is mounted, the chair unit including an upper body support, a seat, and a leg cradle sequentially arranged in one direction and connected to each other; a controller configured to generate a control signal for moving at least one of the upper body support, the seat, and the leg cradle according to first body information of the object; and a driver configured to generate a driving force for moving at least one of the upper body support, the seat, and the leg cradle according to the control signal.

The obstetric and gynecologic diagnosis apparatus may further include a storage configured to store the first body information of the object; and an input interface configured to input identification (ID) information of the object, wherein the first body information of the object is identified by the ID information of the object, and the ID information of the object is at least one of name information of the object, fingerprint information of the object, face information of the object, and an ID code corresponding to the object.

The first body information of the object may be at least one of a gestation period of the object, a number of fetuses carried by the object, a location of a fetus, a weight of the object, a height of the object, a body temperature of the object, an examination history of the object, and a medical history of the object.

User ID information including body information of a user may be input to the input interface, and the controller may generate a control signal for moving at least one of the upper body support, the seat, and the leg cradle according to the first body information of the object and the body information of the user.

The obstetric and gynecologic diagnosis apparatus may further include at least one ultrasound probe configured to transmit an ultrasound signal to the object and receive an ultrasound echo signal from the object, the at least one ultrasound probe being connected to the chair unit to be movable with respect to the chair unit.

The obstetric and gynecologic diagnosis apparatus may further include a diagnosis part including the controller, an input interface, and a display that displays a diagnosis image of the object, the diagnosis part being connected to the chair unit to be movable with respect to the chair unit.

The obstetric and gynecologic diagnosis apparatus may further include an indicator configured to indicate an operating state of the obstetric and gynecologic diagnosis apparatus.

The chair unit may be arranged to be vertically movable with respect to the ground, the upper body support may be connected to the seat to be rotatable about one axis, and the leg cradle may be connected to the seat to be rotatable about the axis.

In a first diagnosis state, the upper body support may be arranged on a same plane as the seat, and the leg cradle may be inclined at an angle of 120° to 180° clockwise with respect to the seat.

In a second diagnosis state, the upper body support, the seat, and the leg cradle may be arranged on one plane.

The leg cradle may include a first cradle and a second cradle on which both legs of the object are respectively placed, and the first cradle and the second cradle may be arranged such that one end of the first cradle is spaced apart from one end of the second cradle.

In a third diagnosis state, the upper body support may be inclined at an angle of 110° to 170° counterclockwise with respect to the seat, and the leg cradle may be arranged on a same plane as the seat.

The driver may generate a driving force that moves the diagnosis part and the at least one ultrasound probe.

The obstetric and gynecologic diagnosis apparatus may further include a probe holder configured to hold the at least one ultrasound probe; and a probe sensor configured to sense whether the at least one ultrasound probe has been held on the probe holder.

The obstetric and gynecologic diagnosis apparatus may further include at least one sensor configured to sense second body information of the object, wherein the controller generates a control signal for moving at least one of the upper body support, the seat, and the leg cradle according to the first body information of the object and the second body information of the object.

The second body information of the object may be at least one of a weight, a body temperature, a sitting state, and a sitting duration time.

Due to manipulation by a user inputting a driving signal to the input interface, at least one of the upper body support, the seat, and the leg cradle may be moved.

According to an aspect of another embodiment, an obstetric and gynecologic diagnosis method includes obtaining first body information of an object; generating a control signal for a chair unit, based on the obtained first body information of the object; changing the chair unit from an initial state to a diagnosis state according to the control signal; inputting diagnosis completion information; and changing the chair unit from the diagnosis state to the initial state.

The obstetric and gynecologic diagnosis method may further include inputting identification (ID) information of the object, wherein the first body information of the object is obtained based on the ID information of the object, and the ID information of the object is at least one of name information of the object, fingerprint information of the object, face information of the object, and an ID code corresponding to the object.

The first body information of the object may be at least one of a gestation period of the object, a number of fetuses carried by the object, a weight of the object, a height of the object, a body temperature of the object, a medical history of the object, and a location of a fetus.

The diagnosis state may be one of first through third diagnosis states. In the first diagnosis state, the upper body support may be arranged on a same plane as the seat, and the leg cradle may be inclined at an angle of 120° to 180° clockwise with respect to the seat. In the second diagnosis state, the upper body support, the seat, and the leg cradle may be arranged on one plane. In the third diagnosis state, the upper body support may be inclined at an angle of 110° to 170° counterclockwise with respect to the seat, and the leg cradle may be arranged on a same plane as the seat.

When a probe has been held on a probe holder for a certain period of time or more, the diagnosis completion information may be input.

The obstetric and gynecologic diagnosis method may further include obtaining second body information of the object by using a sensor, wherein the second body information of the object is at least one of a weight, a body temperature, a sitting state, and a sitting duration time.

The control signal for the chair unit may be generated based on the obtained first body information of the object and the obtained second body information of the object.

The obstetric and gynecologic diagnosis method may further include adjusting the diagnosis state of the chair unit by using an input signal generated by a user.

According to an aspect of another embodiment, an obstetric and gynecologic diagnosis method includes obtaining first body information of an object and body information of a user; generating a control signal for a chair unit, based on the obtained first body information of the object and the obtained body information of the user; changing the chair unit from an initial state to a diagnosis state according to the control signal; inputting diagnosis completion information; and changing the chair unit from the diagnosis state to the initial state.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
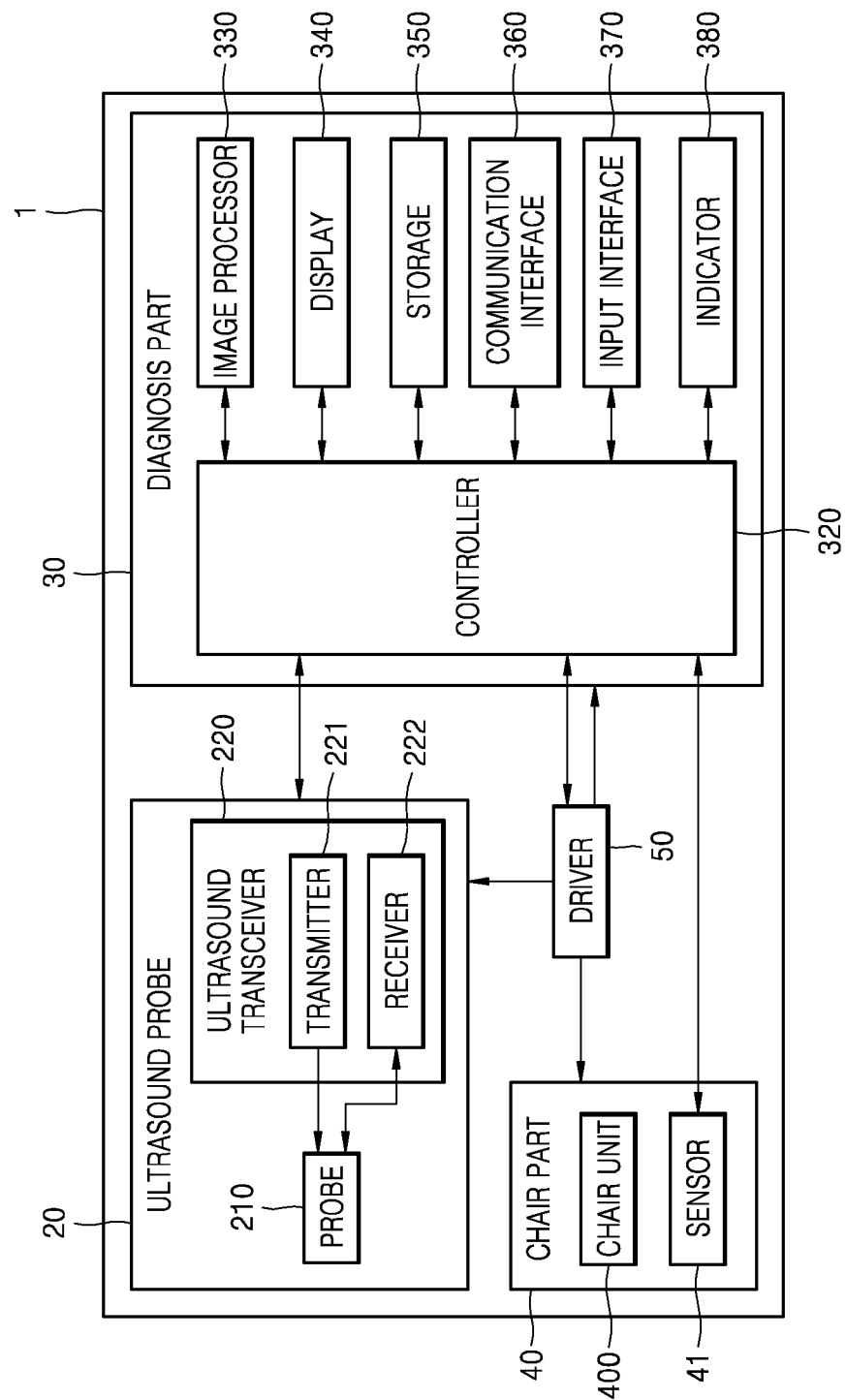
FIG. 1 is a block diagram of a structure of an obstetric and gynecologic diagnosis apparatus according to an embodiment.

The principle of the present disclosure is explained and embodiments are disclosed so that the scope of the present disclosure is clarified and one of ordinary skill in the art to which the present disclosure pertains may implement the present disclosure. The disclosed embodiments may have various forms.

Throughout the specification, like reference numerals or characters refer to like elements. In the specification, all elements of embodiments are not explained, but general matters in the technical field of the present disclosure or redundant matters between embodiments will not be described. Terms 'part' and 'portion' used herein may be implemented using software or hardware, and, according to embodiments, a plurality of 'parts' or 'portions' may be implemented using a single unit or element, or a single 'part' or 'portion' may be implemented using a plurality of units or elements. The operational principle of the present disclosure and embodiments thereof will now be described more fully with reference to the accompanying drawings.

Throughout the specification, the term 'object' is a thing to be imaged, and may include a patient, a mother, a fetus, or a part of a patient, mother, or fetus. For example, the object may include a part of a body organ of a mother, a fetus of the mother, a phantom, or the like.

Throughout the specification, a "user" may be, but is not limited to, a medical expert, such as a medical doctor, a nurse, a medical laboratory technologist, a medical image expert, or the like.

Throughout the specification, an "ultrasound image" refers to an image of an object processed based on ultrasound signals transmitted to the object and reflected therefrom.

Embodiments will now be described more fully hereinafter with reference to the accompanying drawings.

Figure 2:
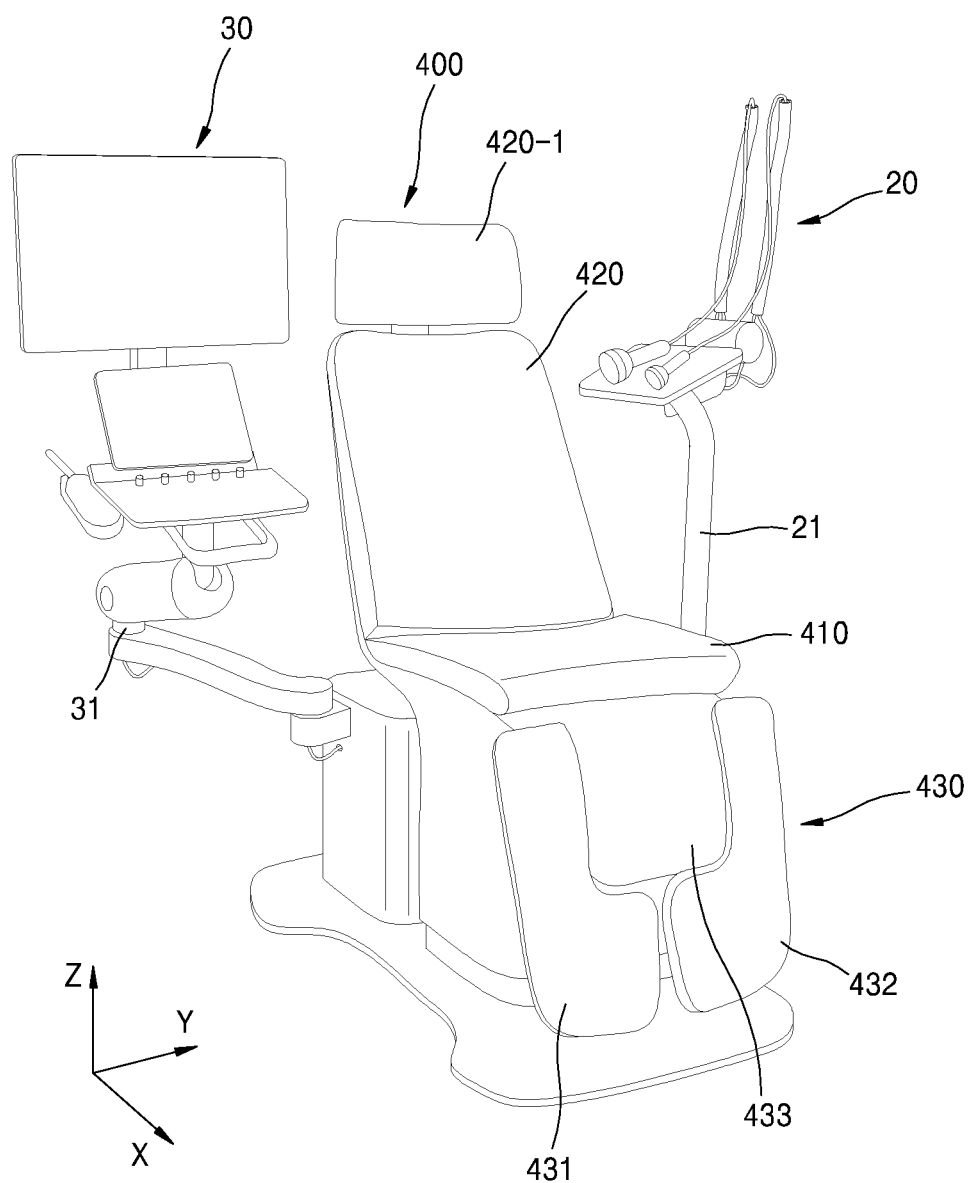
FIG. 2 is a perspective view of the obstetric and gynecologic diagnosis apparatus of FIG. 1.

FIG. 1 is a block diagram of a structure of an obstetric and gynecologic diagnosis apparatus 1 according to an embodiment. FIG. 2 is a perspective view of the obstetric and gynecologic diagnosis apparatus 1.

Referring to FIGS. 1 and 2, the obstetric and gynecologic diagnosis apparatus 1 may include an ultrasound probe 20 including an ultrasound transceiver, a diagnosis part 30 that may be used by a user to manipulate the obstetric and gynecologic diagnosis apparatus 1 to diagnose an object, and a chair part 40 on which the object is mountable.

According to an embodiment, the ultrasound probe 20 may include a probe 210 and an ultrasound transceiver 220 that transmits or receives ultrasound waves. The probe 210 may include a plurality of transducers. The plurality of transducers may transmit ultrasound signals to an object according to a transmission signal applied by a transmitter 221 included in the ultrasound transceiver 220. The plurality of transducers may receive ultrasound signals reflected by the object and may form a reception signal. The probe 210 may be integrated with the obstetric and gynecologic diagnosis apparatus 1, or may be separate from the obstetric and gynecologic diagnosis apparatus 1 and may be connected thereto via wired and/or wireless communication. In addition, the obstetric and gynecologic diagnosis apparatus 1 may include one probe 210 or a plurality of probes 210 according to embodiments.

According to an embodiment, the diagnosis part 30 may include a controller 320 for controlling the obstetric and gynecologic diagnosis apparatus 1, an image processor 330 for processing a received signal into an image, a display 340 for outputting the image, a storage 350, a communication interface 360, and an input interface 370.

The controller 320 may control all operations of the obstetric and gynecologic diagnosis apparatus 1 and signal transfer among the internal components of the obstetric and gynecologic diagnosis apparatus 1. The controller 320 may include a memory configured to store programs or data for performing functions of the obstetric and gynecologic diagnosis apparatus 1, and a processor configured to process the programs or the data. The controller 320 may receive a control signal from the input interface 370 or an external device to control an operation of the obstetric and gynecologic diagnosis apparatus 1.

The signal processor 330 generates an ultrasound image by using ultrasound data generated by a receiver 222 included in the ultrasound transceiver 220.

The display 340 may display the generated ultrasound image and various pieces of information processed in the obstetric and gynecologic diagnosis apparatus 1. The display 340 may include one display or a plurality of displays according to embodiments, for example, a first display for the user and a second display for the object. In this case, the display may be coupled with a touch panel and thus may be implemented as a touch screen.

The storage 350 may store, for example, various pieces of data or various programs for driving and controlling the obstetric and gynecologic diagnosis apparatus 1, input/output ultrasound data, obtained ultrasound images, identification (ID) information and body information of the object, and ID information and body information of the user.

Herein, the ID information of the object and the user means at least one of all types of information capable of identifying the object and the user, for example, a name, a resident registration number, a birth date, a personal ID number, a personal ID code, and biometric information (e.g., a face, an iris, and a fingerprint). Herein, the body information of the object means all pieces of body information of the object necessary for an obstetric and gynecologic treatment, for example, a gestation period of a pregnant woman, the number of fetuses carried by the pregnant woman, the location of a fetus, the weight of the pregnant woman, the height of the pregnant woman, the body temperature of the pregnant woman, the examination history of the pregnant woman, and the medical history of the pregnant woman. Herein, the body information of the user means all pieces of body information of the user necessary during a diagnosing process, for example, a surgical procedure posture of a surgical operator, the height and sitting height thereof, the arm length thereof, and an eye position thereof.

The obstetric and gynecologic diagnosis apparatus 1 may include the communication interface 360 and may be connected to external devices, such as, a central server, a medical apparatus, and a portable device (smartphone, tablet personal computer (PC), wearable device, etc.), via the communication interface 360.

The communication interface 360 may include one or more components that enable communication with an external device. For example, the communication interface 360 may include at least one of a short distance communication module, a wired communication module, and a wireless communication module.

For example, the communication interface 360 may transmit the ID information of the object and the user to an external device, for example, a central server, and the external device transmits data related to body information of the object and the user according to the received ID information of the object and the user to the controller 320 so that the controller 320 controls the obstetric and gynecologic diagnosis apparatus 1 according to the received data related to the body information of the object and the user. The external device may include a recording medium having recorded thereon the data related to the body information of the object and the user.

The input interface 370 may receive a user input for controlling the obstetric and gynecologic diagnosis apparatus 1. For example, the user may input, for example, the ID information of the object, the ID information of the user, or a manipulation signal (which will be described later below) for adjusting a position of the chair part 40, to the input interface 370. The user input may include, but is not limited to, an input for manipulating a button, a key pad, a mouse, a trackball, a jog switch, a knob, or the like, an input for touching a touch pad or a touch screen, a voice input, a motion input, and a biometric data input.

An indicator 380 is a display capable of displaying an operating state of the obstetric and gynecologic diagnosis apparatus 1 to the object. For example, the indicator 380 may display various operating states of the obstetric and gynecologic diagnosis apparatus 1 by using a change in the color of a visual indicator, for example, a light-emitter, as shown in FIG. 2, or may display the various operating states of the obstetric and gynecologic diagnosis apparatus 1 by using an auditory indicator. However, embodiments of the present disclosure are not limited thereto, and the indicator 380 may be implemented by using the other display methods, such as a character and an image.

According to an embodiment, the chair part 40 may include a chair unit 400 on which the object is mountable, and at least one sensor 41 capable of obtaining body information of the object. The chair unit 400 is thick enough that the object can be seated thereon. A length direction of the chair unit 400 is parallel to a length or height direction of the object. The chair unit 400 may be fixed to the floor or may be movable on the floor. For example, the chair unit 400 is vertically movable to ascend or descend the object, and may be inclined to adjust a diagnosis angle with respect to the object. The movement of the chair unit 400 to diagnose the object will be described later in more detail with reference to FIG. 3A.

According to an embodiment, the chair unit 400 may include a seat 410, and an upper body support 420 of which an inclination is adjustable with respect to the seat 410. The seat 410 supports a lower body of the object, and the upper body support 420 supports an upper body of the object. The upper body support 420 may include a head support 420-1 for supporting the head of the object. The head support 420-1 is fixed to the upper body support 420 to be detachable therefrom, and may be separated from the upper body support 420 according to a diagnosis state. The chair unit 400 may also include a leg cradle 430 for supporting the legs of the object. According to an embodiment, the leg cradle 430 may include a first cradle 431 and a second cradle 432 capable of respectively supporting both legs of the object, namely, the right leg and the left leg. A cover support 433, which is detachable, may be arranged between the first cradle 431 and the second cradle 432. A secretion container 450 of FIG. 8C for temporarily storing secretions of the object produced while the object is being diagnosed may be arranged below the cover support 433. The cover support 433 may be fixed between the first cradle 431 and the second cradle 432 to support the object or may be separated from the chair unit 400 to expose the secretion container 450, according to diagnosis states of the object.

For example, the user may adjust the angle of the upper body support 420 with respect to the seat 410 or adjust the angle of the leg cradle 430 with respect to the seat 410, according to diagnosis states of the object. The first cradle 431 and the second cradle 432 included in the leg cradle 430 may be adjusted at various angles to be spaced apart from each other according to a diagnosis state of the object.

The sensor 41 is a sensing device capable of sensing the state of the object mounted on the chair unit 400. For example, the sensor 41 may include a weight sensor capable of measuring measured information of the object, for example, the weight of the object, in real time, a temperature sensor capable of sensing a temperature change of the object, a time sensor capable of sensing and calculating a seating duration time, or an operation sensor capable of sensing a sudden seating state change of the object. Accordingly, the sensor 41 may sense measured information of the object and a sudden seating state change of the object occurring during a diagnosis of the object, and may transmit the measured information of the object and location movement information of the object to the controller 320.

Referring back to FIG. 1, the driver 50 may generate a driving force capable of moving the ultrasound probe 20, the diagnosis part 30, and the chair part 40 according to the control signal of the controller 320. When the object is a mother who is carrying a fetus, her appearance rapidly changes according to growth of the fetus, and diagnostic items also change according to the growth of the fetus. According to a change in a diagnostic posture of the mother due to changes in the external appearance of the mother and the diagnostic items, the shape and location of the chair part 40, on which the mother is seated to receive an obstetric and gynecologic diagnosis, need to be changed, and those of the ultrasound probe 20 and the diagnosis part 30 also need to be changed in order to provide usage convenience to the user. The formation of the control signal capable of controlling the driver 50 according to the body information of the object and the body information of the user, and the automatic movement of the ultrasound probe 20, the diagnosis part 30, and the chair part 40 in accordance with the diagnosis state of the object will now be described in more detail.

Figure 3A:
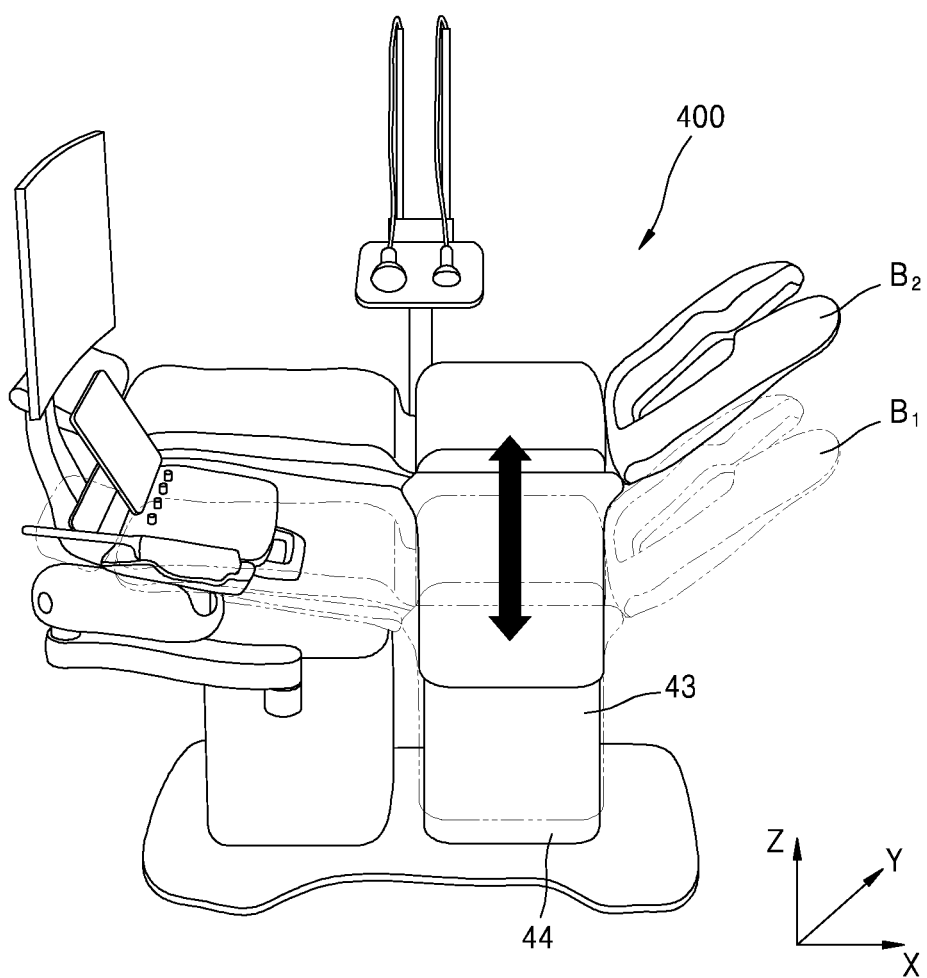
FIG. 3A is a perspective view of the obstetric and gynecologic diagnosis apparatus for showing a vertical movement of a chair unit included in the obstetric and gynecologic diagnosis apparatus, according to an embodiment.
Figure 3B:
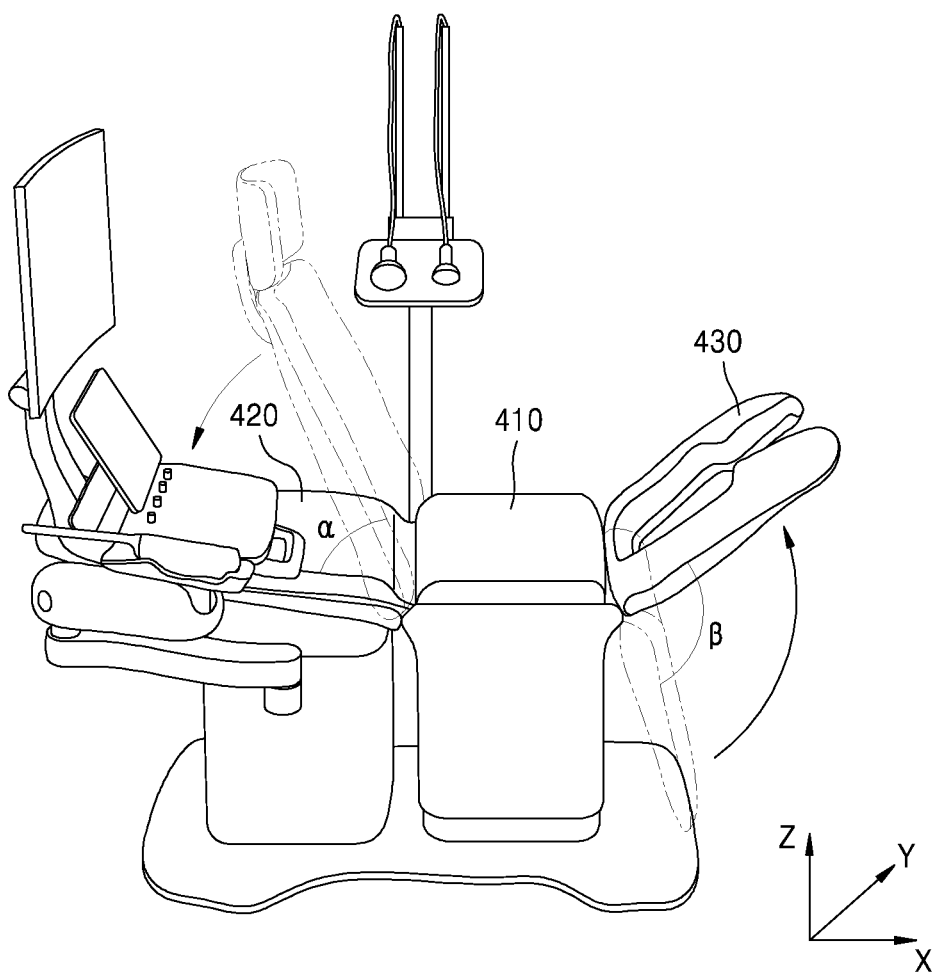
FIG. 3B is a perspective view of the obstetric and gynecologic diagnosis apparatus for showing rotational movements of an upper body support and a leg cradle included in the obstetric and gynecologic diagnosis apparatus, according to an embodiment.

FIG. 3A is a perspective view of the obstetric and gynecologic diagnosis apparatus 1 for showing a vertical movement of the chair unit 400. FIG. 3B is a perspective view of the obstetric and gynecologic diagnosis apparatus 1 for showing rotational movements of the upper body support 420 and the leg cradle 430.

According to an embodiment, the user may perform an obstetric and gynecologic diagnosis using the obstetric and gynecologic diagnosis apparatus 1 while standing or sitting according to diagnosis states of the object. In addition, the height of an object and a ratio between the upper body and the lower body of the object may differ according to individuals. Thus, according to obstetric and gynecologic diagnosis states of the object and the body information of the object and the user, the object that is being diagnosed may be mounted on the chair unit 400 to be at different locations from the ground or to maintain various postures.

Referring to FIG. 3A, the chair unit 400 may move vertically with respect to the ground. The ground refers to a support surface on which a bottom of the obstetric and gynecologic diagnosis apparatus 1 is supported, for example, the floor of a building on which the obstetric and gynecologic diagnosis apparatus 1 is supported or the floor of a diagnosis room where an obstetric and gynecologic diagnosis is performed.

For example, when the chair unit 400 is arranged at a first location B1 that is relatively low from the ground, a slide part 43 fixed to the bottom of the chair unit 400 may be moved downwards along a Z-axis by a slide guide part 44 fixed to the ground. At this time, the driver 50 of FIG. 1 may generate a driving force according to the control signal received from the controller 320 and automatically move the chair unit 400. Accordingly, the object mounted on the chair unit 400 may also be moved downwards along the Z-axis and be positioned at a low location from the ground.

On the other hand, when the chair unit 400 is arranged at a second location B2 that is relatively high from the ground, the slide part 43 fixed to the bottom of the chair unit 400 may be moved upwards along the Z-axis by the slide guide part 44 fixed to the ground. At this time, the driver 50 of FIG. 1 may generate a driving force according to the control signal received from the controller 320 and automatically move the chair unit 400. Accordingly, the object mounted on the chair unit 400 may also be moved upwards along the Z-axis and be positioned at a high location from the ground.

Referring to FIG. 3B, the upper body support 420 and the leg cradle 430 of the chair unit 400 may rotate with respect to the seat 410 such that the object may maintain various postures.

For example, the upper body support 420 may rotate about an axis Y with respect to the seat 410. For example, the upper body support 420 may be rotated to have a first angle $\alpha$ that is no less than 90° and no more than 180°, with respect to the seat 410. At this time, the driver 50 of FIG. 1 may generate a driving force according to the control signal received from the controller 320 and transmit the driving force to a driving force transmitter (not shown) arranged on the bottom of the chair unit 410 to thereby automatically rotate the upper body support 420. Accordingly, the upper body of the object mounted on the chair unit 400 may also be rotated with respect to the lower body of the object supported by the chair unit 410 and thus be positioned at a diagnosis location where the object sits or lies.

The leg cradle 430 may rotate about the axis Y with respect to the seat 410. For example, the leg cradle 430 may be rotated to have a second angle $\beta$ that is no less than 100° and no more than 270° with respect to the seat 410. At this time, the driver 50 of FIG. 1 may generate a driving force according to the control signal received from the controller 320 and transmit the driving force to the driving force transmitter arranged on the bottom of the chair unit 410 to thereby automatically rotate the leg cradle 430. Accordingly, the legs of the object mounted on the chair unit 400 may be rotated to be positioned at a certain diagnosis location.

Figure 4A:
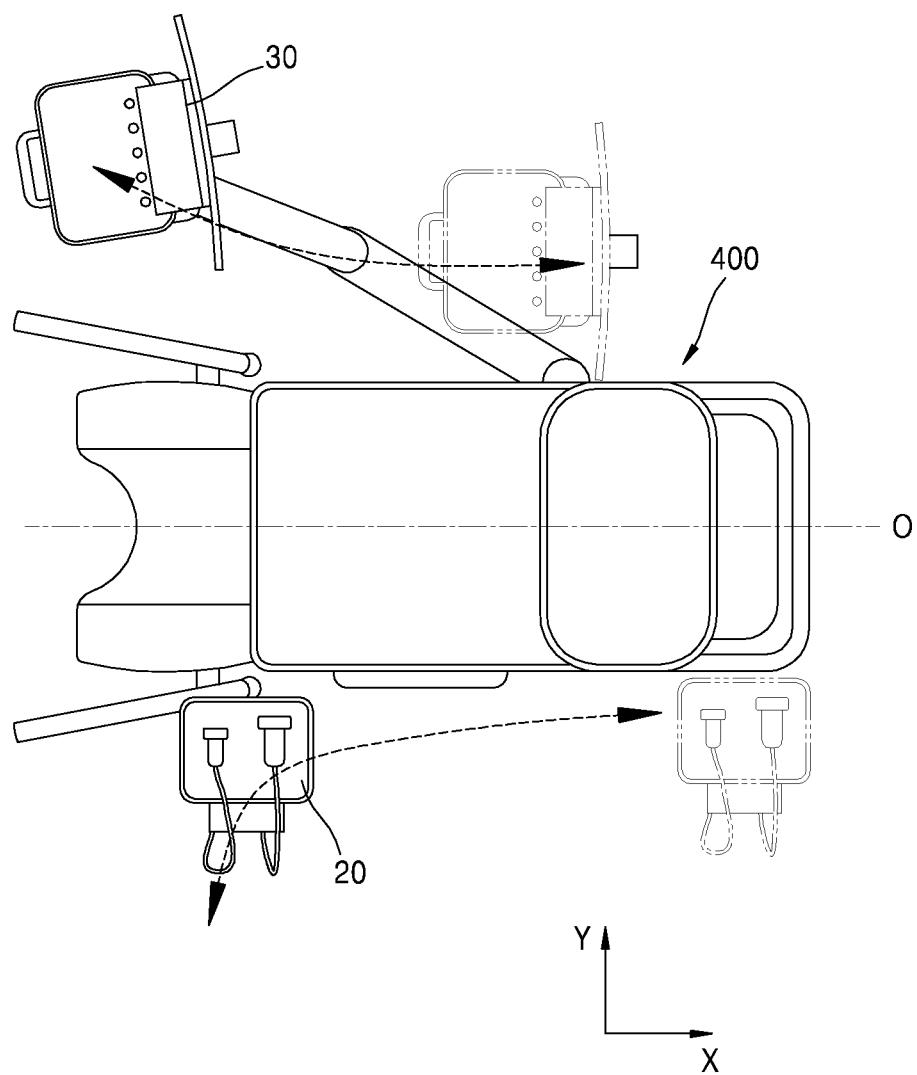
FIG. 4A is a plan view of the obstetric and gynecologic diagnosis apparatus for showing planar movements of the ultrasound probe and the diagnosis part, according to an embodiment.
Figure 4B:
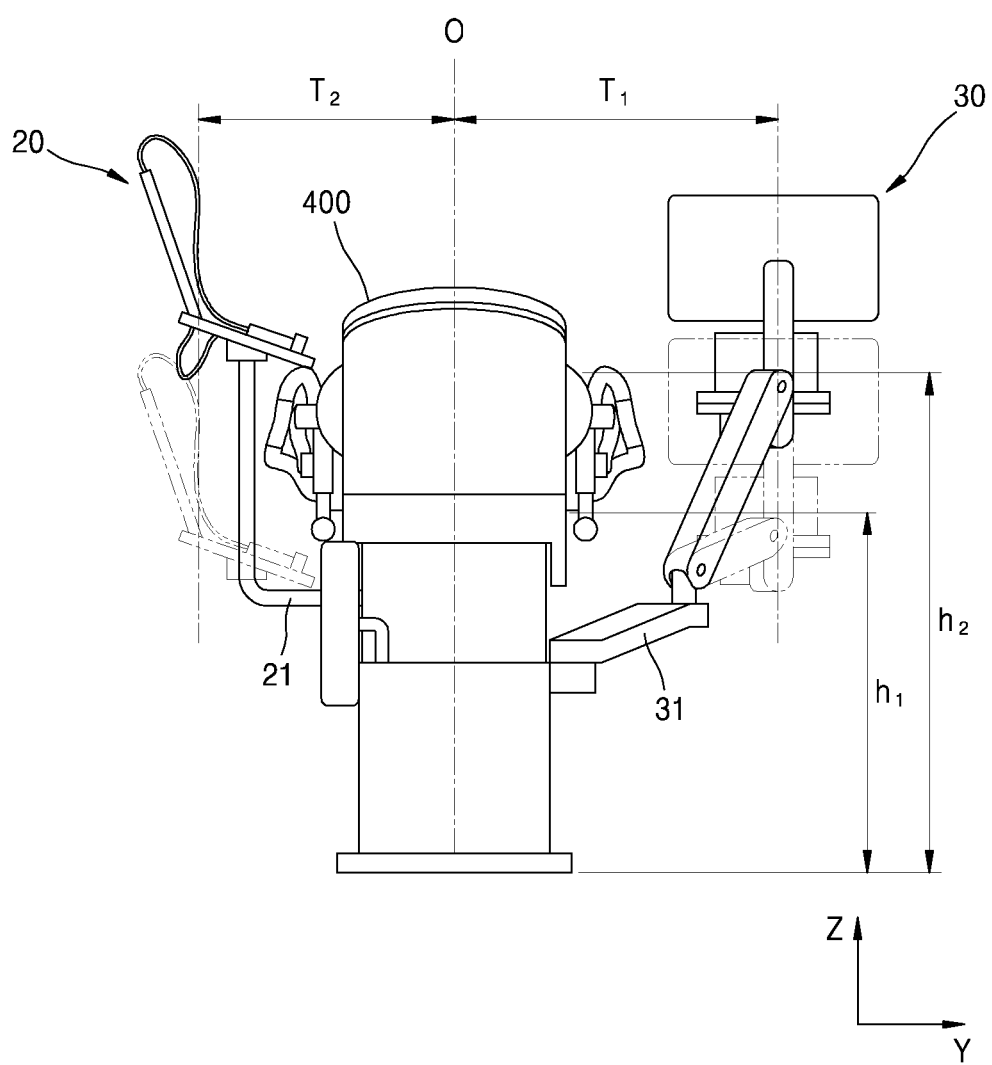
FIG. 4B is a side view of the obstetric and gynecologic diagnosis apparatus for showing vertical movements of the ultrasound probe and the diagnosis part, according to an embodiment.

FIG. 4A is a plan view of the obstetric and gynecologic diagnosis apparatus 1 for showing planar movements of the ultrasound probe 20 and the diagnosis part 30. FIG. 4B is a side view of the obstetric and gynecologic diagnosis apparatus 1 for showing vertical movements of the ultrasound probe 20 and the diagnosis part 30.

According to an embodiment, the user may perform an obstetric and gynecologic diagnosis using the obstetric and gynecologic diagnosis apparatus 1 by being located adjacent to the upper body or the lower body of the object according to diagnosis states. Accordingly, to improve the usage convenience of the user, the locations of the ultrasound probe 20 and the diagnosis part 30 used by the user may vary according to obstetric and gynecologic diagnosis states of the object and the body information of the user.

Referring to FIGS. 4A and 4B, the ultrasound probe 20 and the diagnosis part 30 may be arranged on opposite sides of the chair unit 400. In this case, the ultrasound probe 20 and the diagnosis part 30 may be connected to each other to be movable relative to the chair unit 400. For example, the ultrasound probe 20 and the diagnosis part 30 arranged on opposite sides of the chair unit 400 may be spaced apart from a center line of the chair unit 400 parallel to a length direction thereof by distances T2 and T1, respectively, for example, by distances that are no less than 30 cm and no more than 70 cm, according to a diagnosis state of the object. In this case, the ultrasound probe 20 and the diagnosis part 30 may move from above the upper body support 420 to below the leg cradle 430 in an X-axis direction. The ultrasound probe 20 and the diagnosis part 30 may be arranged to be spaced apart from the ground by heights h1 and h2, for example, heights that are no less than 70 cm and no more than 120 cm, according to diagnosis states of the object. At this time, the driver 50 of FIG. 1 may generate a driving force according to the control signal received from the controller 320 and transmit the driving force to a first connector 21 and a second connector 31 each implemented as a plurality of link parts, to thereby automatically move the ultrasound probe 20 and the diagnosis part 30. Accordingly, the ultrasound probe 20 and the diagnosis part 30 may be positioned at diagnosis locations corresponding to each diagnosis state.

Figure 5A:
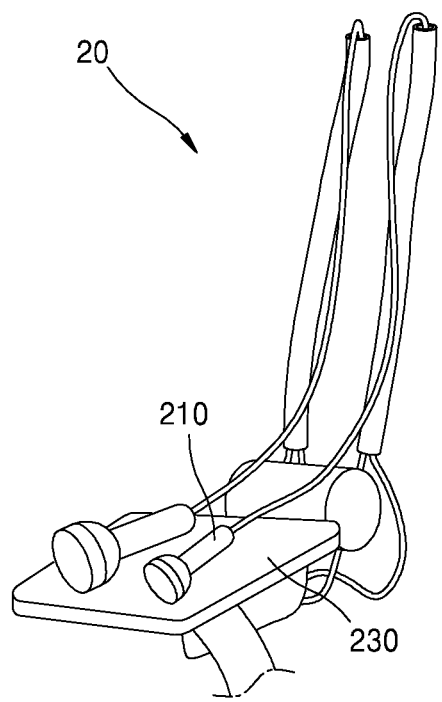
FIG. 5A is a perspective view of the ultrasound probe and a probe holder according to an embodiment.
Figure 5B:
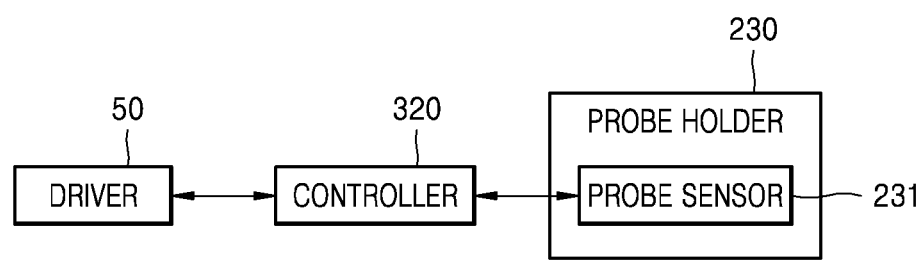
FIG. 5B is a block diagram showing some components of an obstetric and gynecologic diagnosis apparatus according to an embodiment.

FIG. 5A is a perspective view of the ultrasound probe 20 and a probe holder 230 according to an embodiment. FIG. 5B is a block diagram showing some components of an obstetric and gynecologic diagnosis apparatus according to an embodiment.

Referring to FIGS. 5A and 5B, the ultrasound probe 20 may further include the probe holder 230 capable of holding the probe 210, in addition to the probe 210 and the ultrasound transceiver 220. The user may use the probe 210 to diagnose the object, and may hold the probe 210 on the probe holder 230 after the diagnosis is interrupted or completed.

The probe holder 230 may include a probe sensor 231 that detects whether the probe 210 has been held on the probe holder 230. The probe sensor 231 may be arranged on at least one of a plurality of internal walls of the probe cradle 230, but the arrangement of the probe sensor 231 is not limited thereto. For example, the probe sensor 231 may be a weight sensor that senses the weight of the probe 210, a piezoelectric sensor or micro-switch pressed by the probe 210, or an optical sensor. For example, when the probe sensor 231 senses that the probe 210 is held on the probe holder 230 for a certain period of time, for example, 60 seconds or more, it may be recognized that the diagnosis of the object has been completed.

Figure 6:
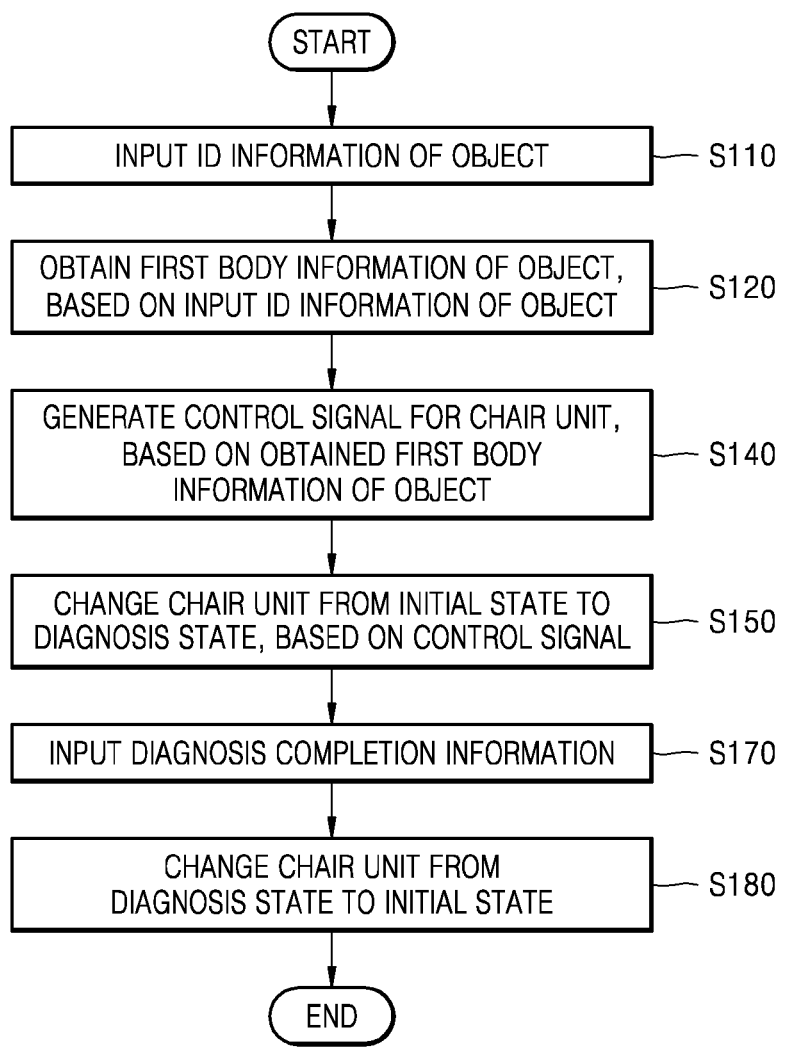
FIG. 6 is a flowchart of an obstetric and gynecologic diagnosis method according to an embodiment.
Figure 7A:
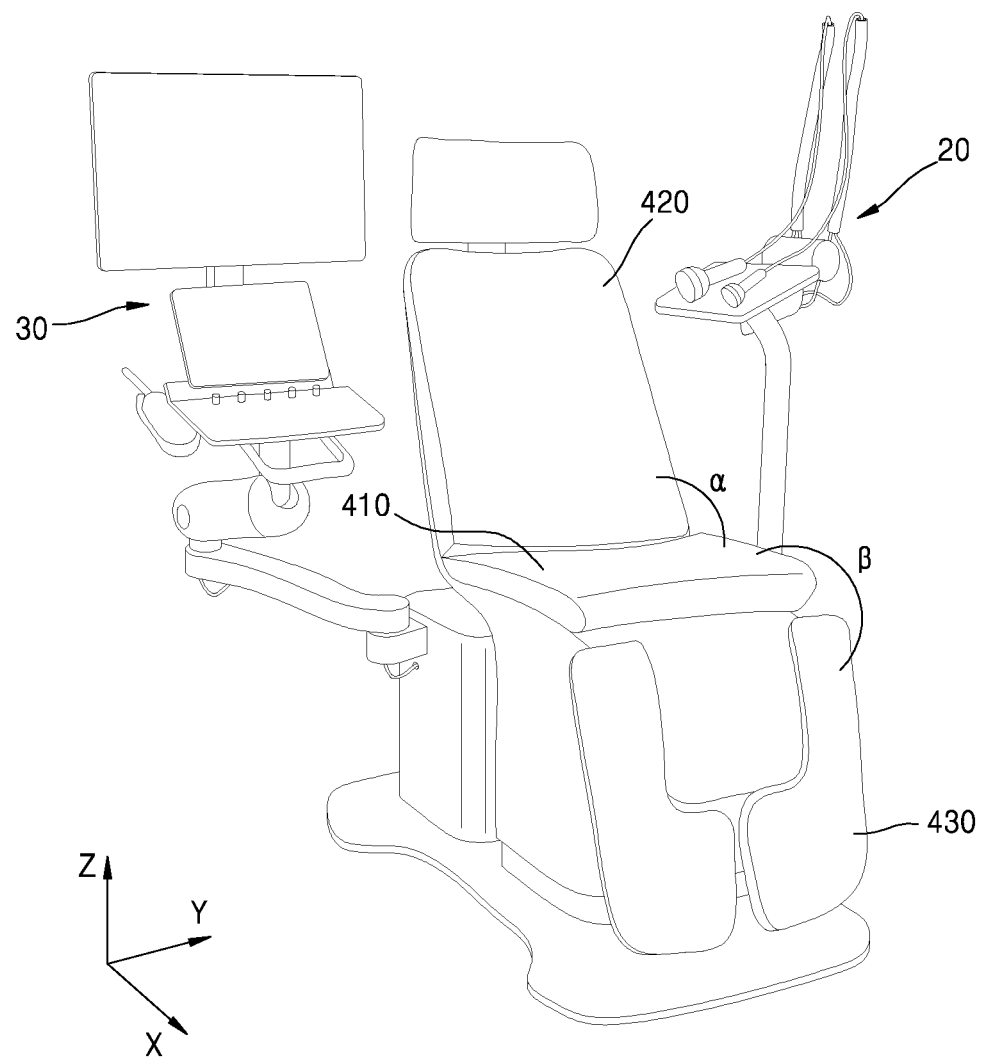
FIGS. 7A to 7C are respectively a perspective view, a side view, and a plan view of the obstetric and gynecologic diagnosis apparatus in an initial state, according to an embodiment.
Figure 7B:
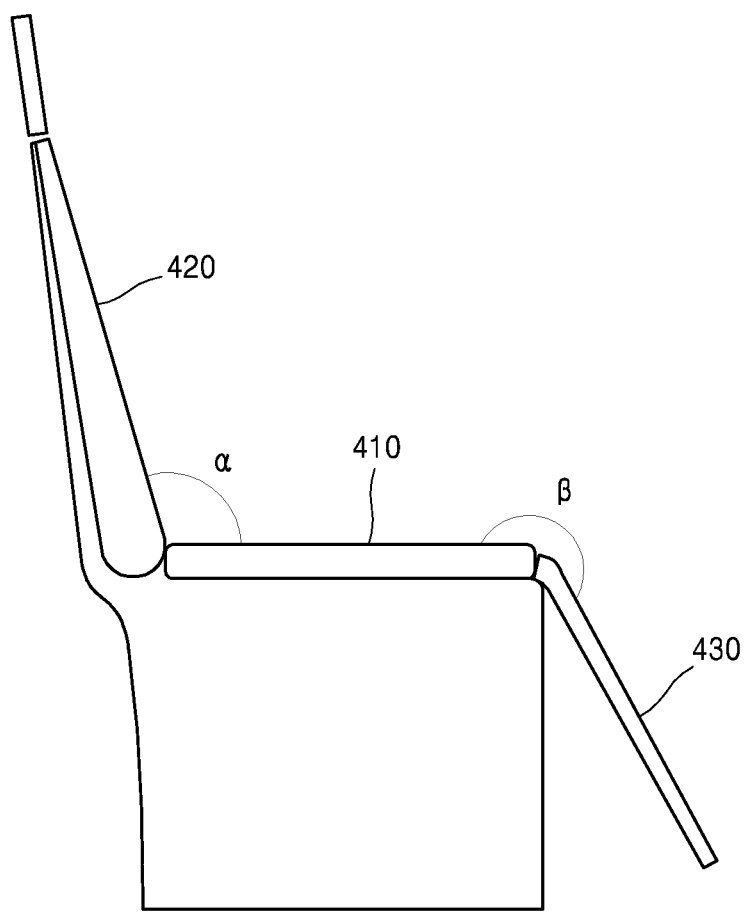
Figure 7C:
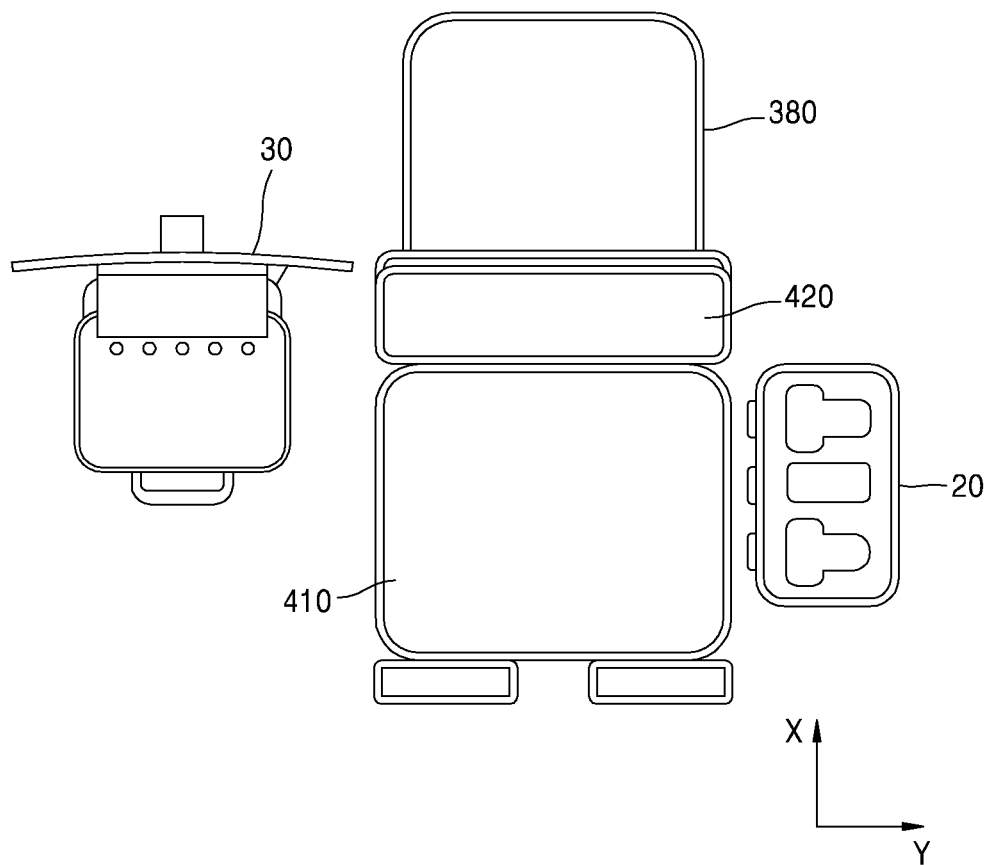
Figure 8A:
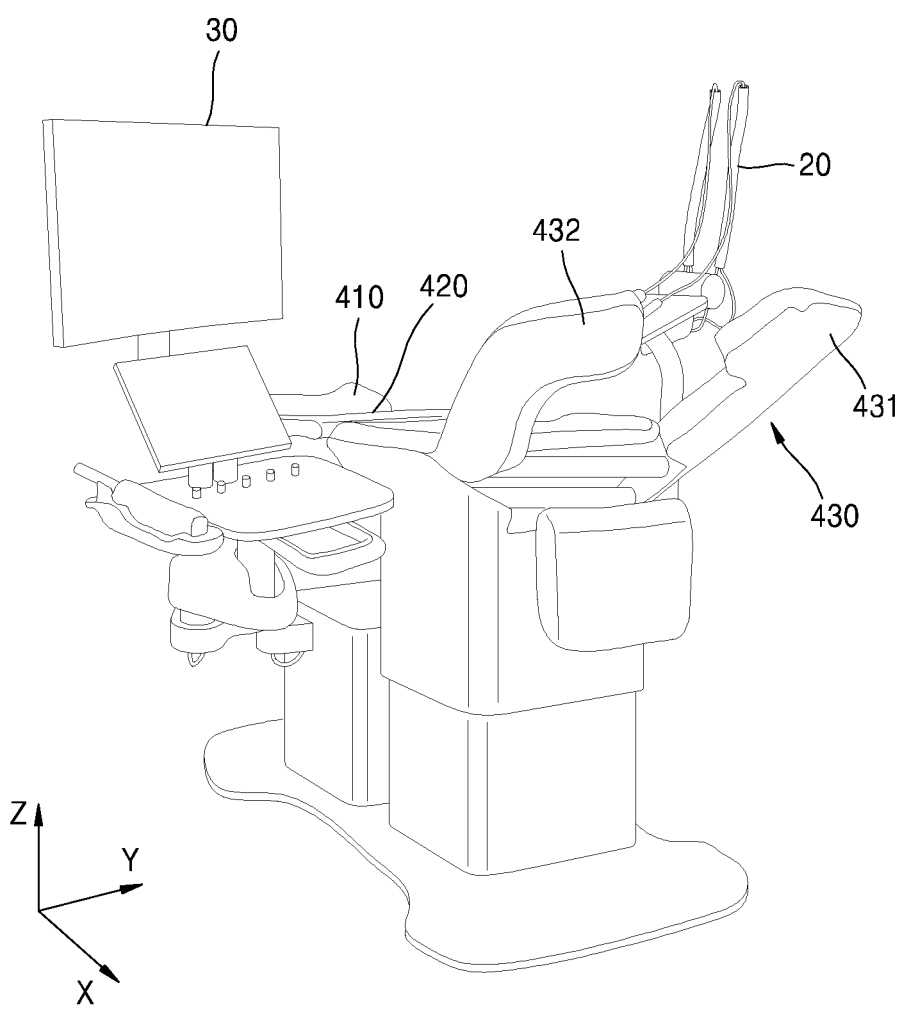
FIGS. 8A to 8C are respectively a perspective view, a side view, and a plan view of the obstetric and gynecologic diagnosis apparatus in a first diagnosis state, according to an embodiment.
Figure 8B:
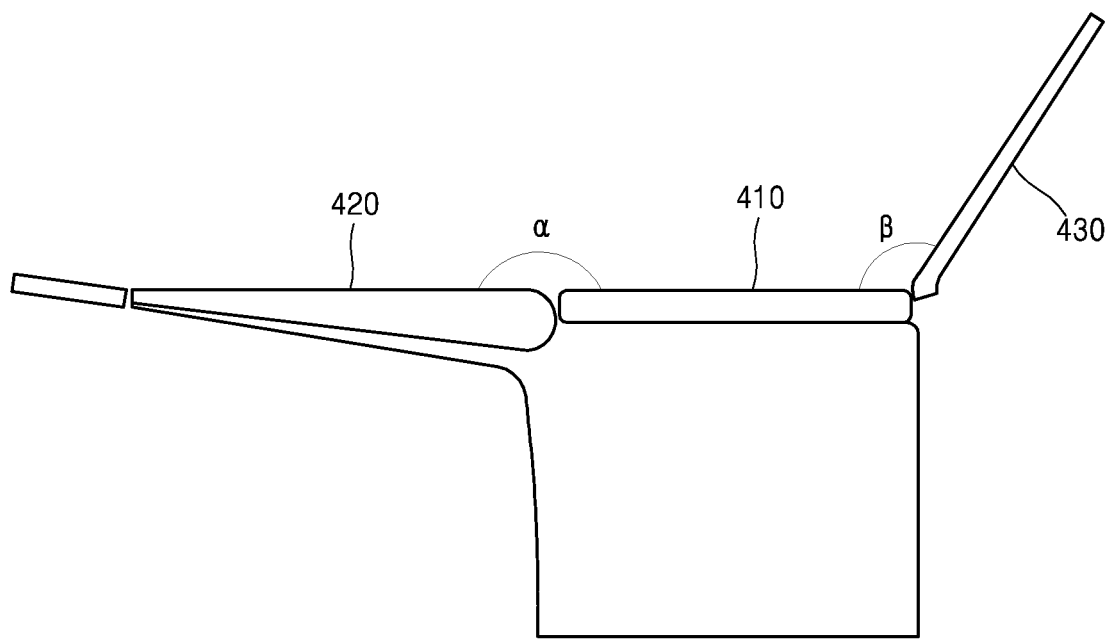
Figure 8C:
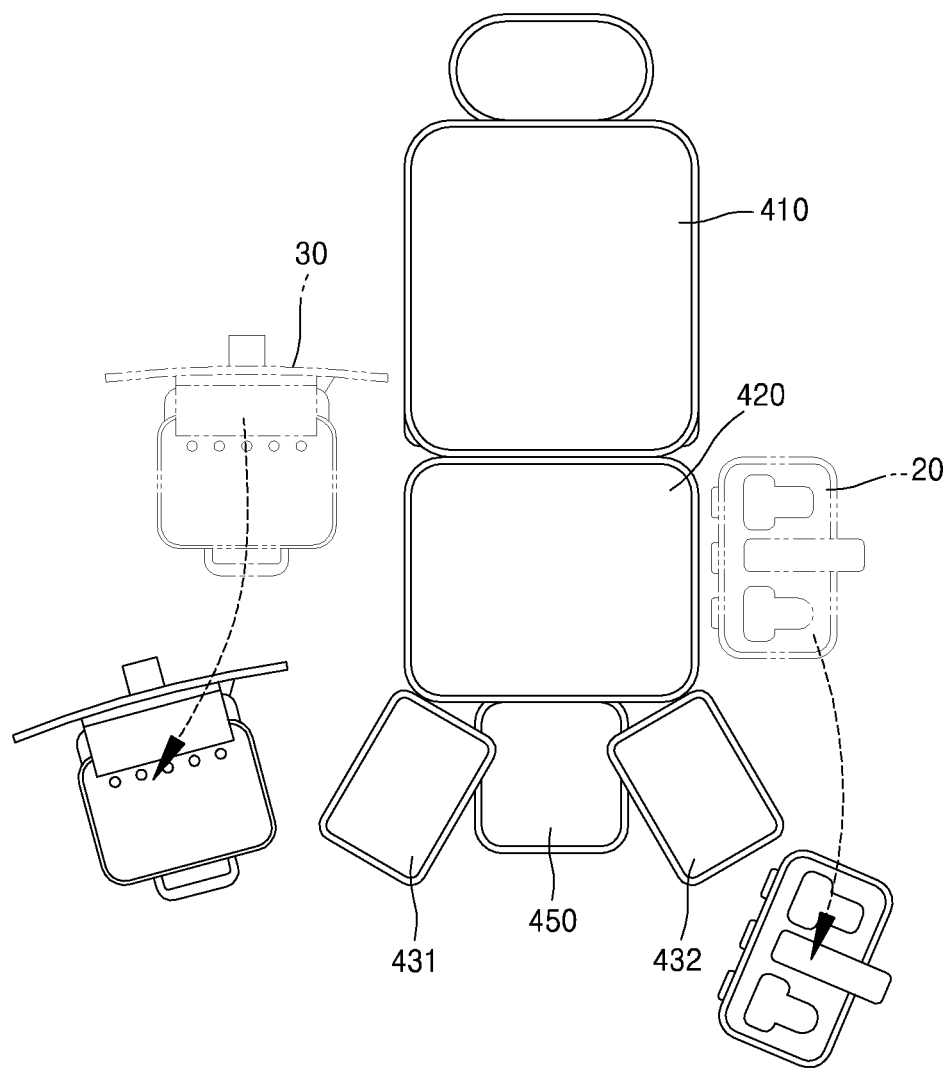
Figure 9A:
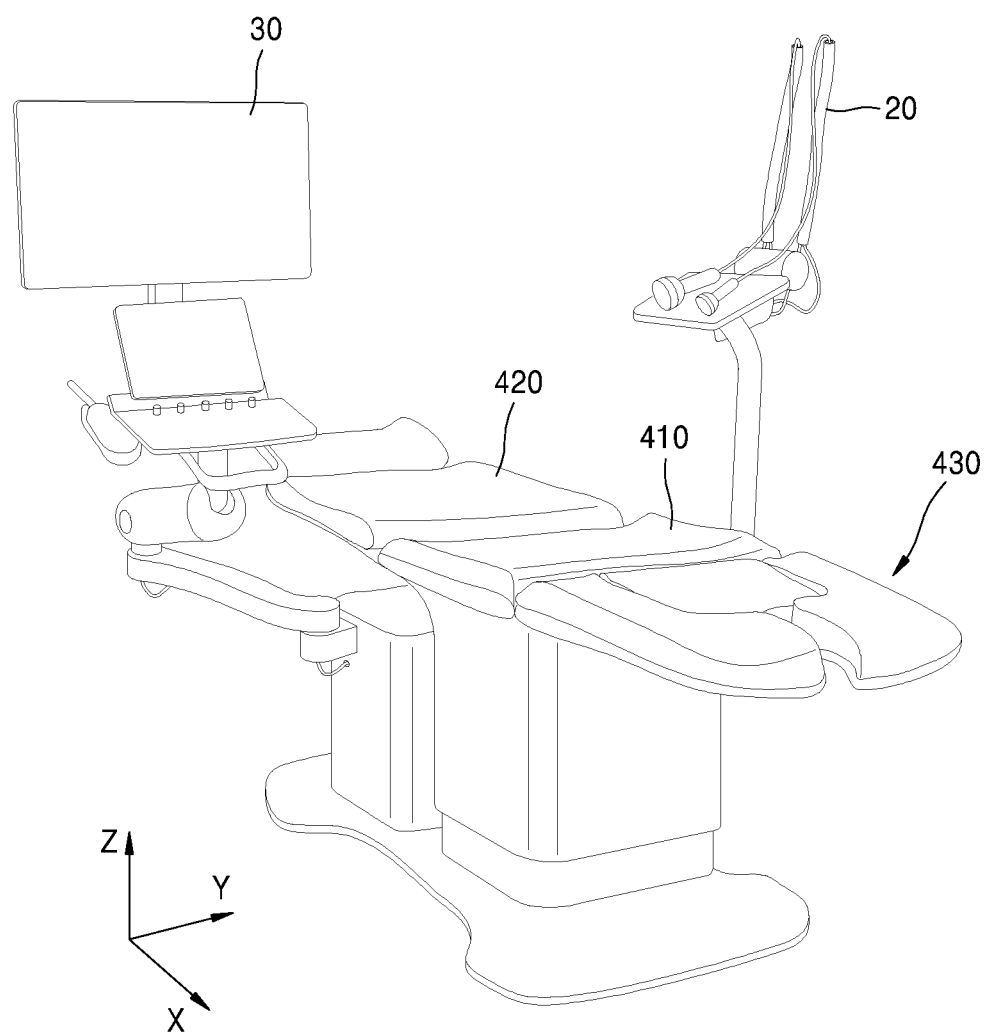
FIGS. 9A and 9B are respectively a perspective view and a plan view of the obstetric and gynecologic diagnosis apparatus in a second diagnosis state, according to an embodiment.
Figure 9B:
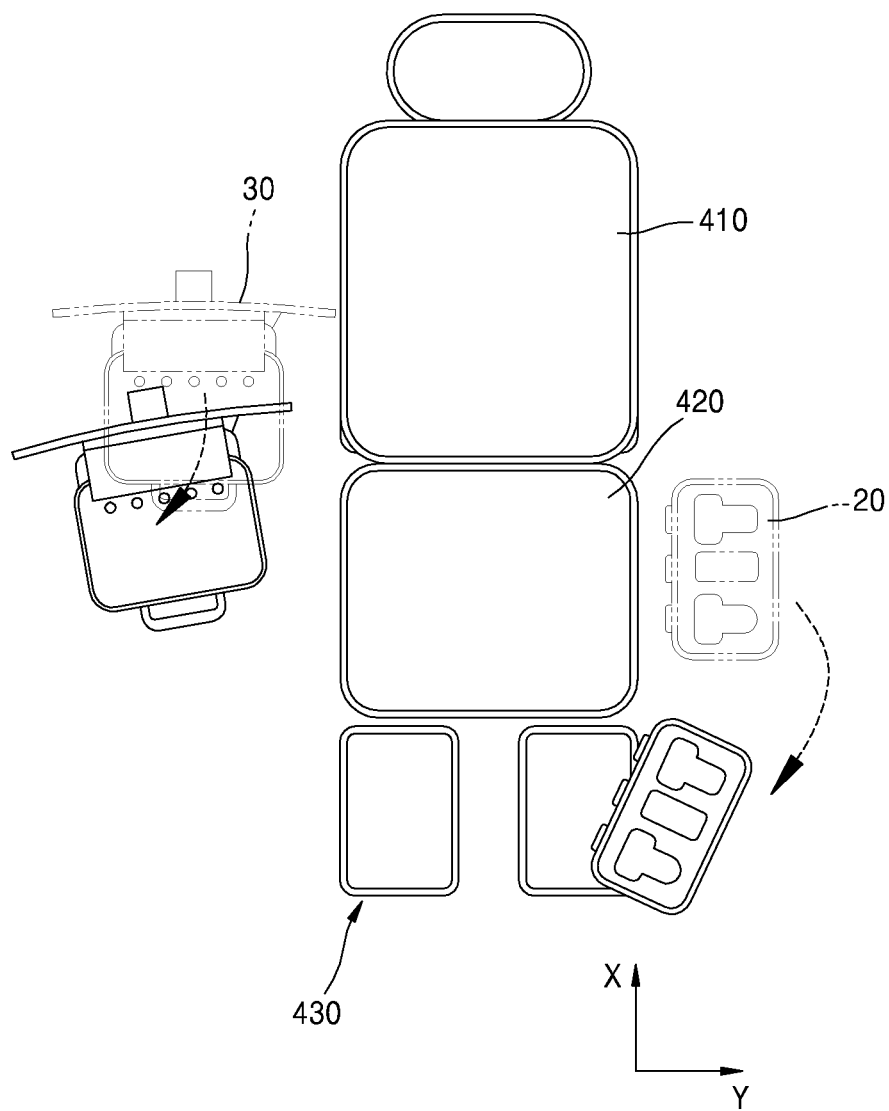
Figure 10A:
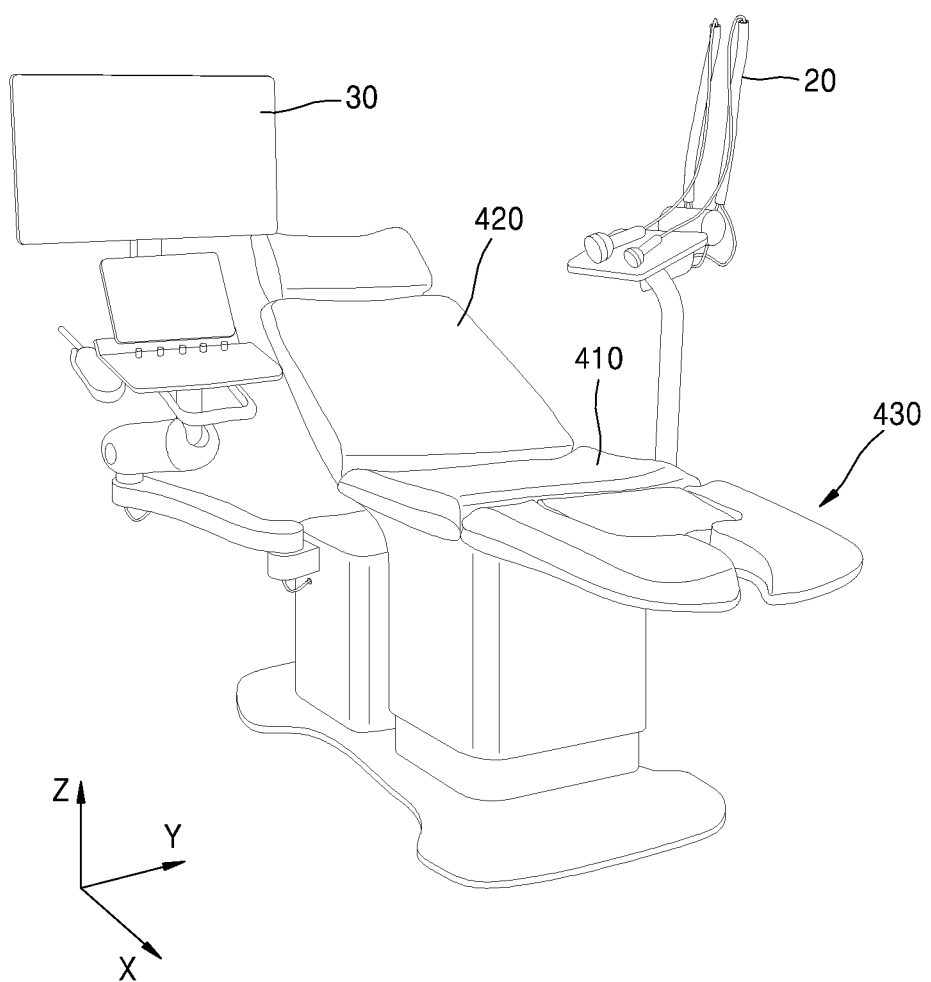
FIGS. 10A to 10C are respectively a perspective view, a side view, and a plan view of the obstetric and gynecological diagnosis apparatus in a third diagnosis state, according to an embodiment.
Figure 10B:
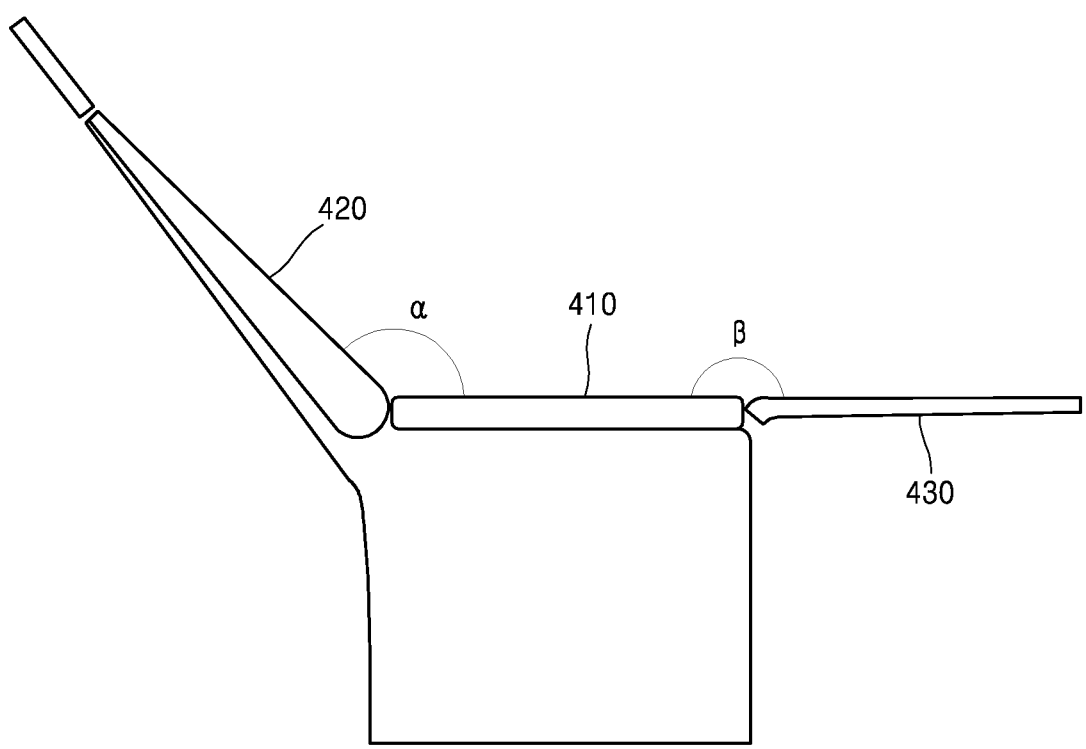
Figure 10C:
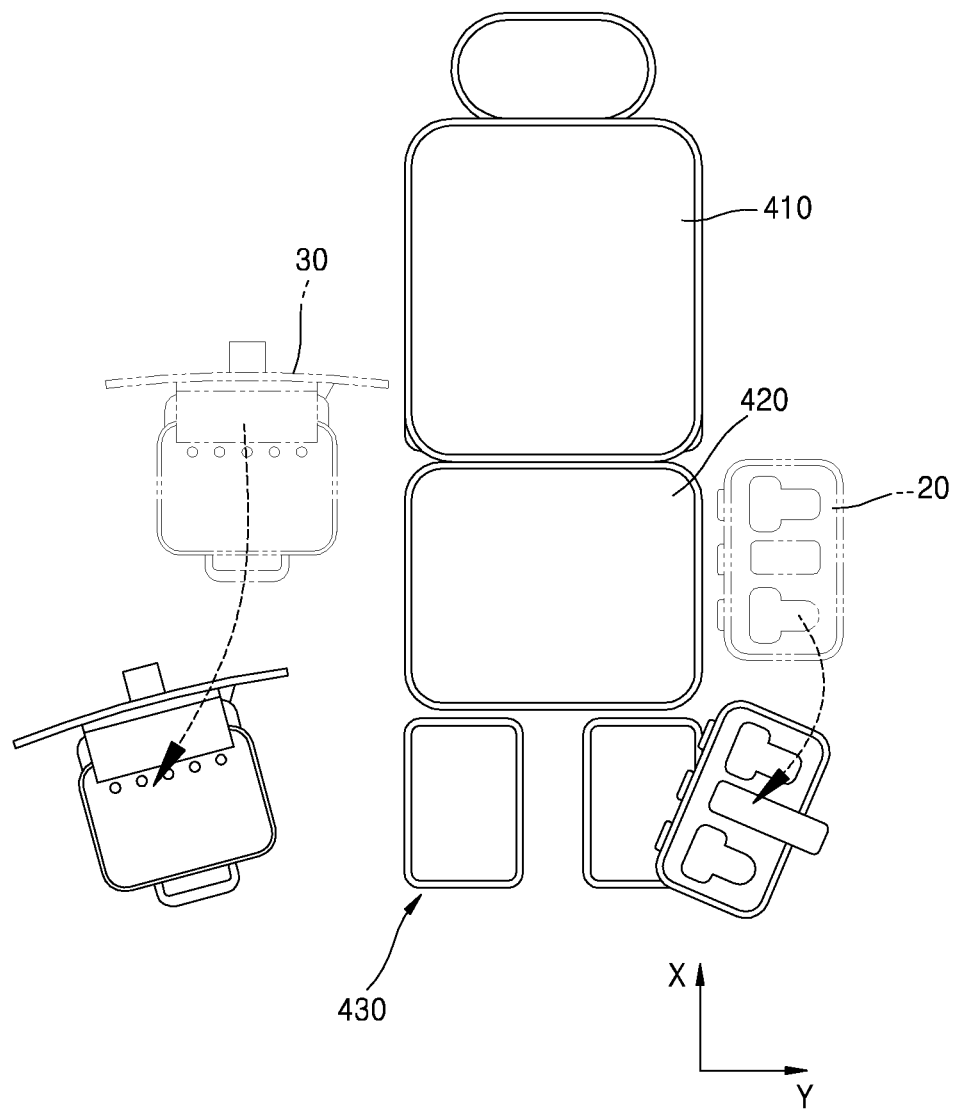

FIG. 6 is a flowchart of an obstetric and gynecologic diagnosis method according to an embodiment. FIGS. 7A to 7C are respectively a perspective view, a side view, and a plan view of the obstetric and gynecologic diagnosis apparatus 1 in an initial state, according to an embodiment. FIGS. 8A to 8C are respectively a perspective view, a side view, and a plan view of the obstetric and gynecologic diagnosis apparatus 1 in a first diagnosis state, according to an embodiment. FIGS. 9A and 9B are respectively a perspective view and a plan view of the obstetric and gynecologic diagnosis apparatus 1 in a second diagnosis state, according to an embodiment. FIGS. 10A to 10C are respectively a perspective view, a side view, and a plan view of the obstetric and gynecologic diagnosis apparatus 1 in a third diagnosis state, according to an embodiment.

Referring to FIG. 6, in operation S110, the ID information of the object is input via the input interface 370 included in the diagnosis part 30. For example, the ID information of the object means, as described above, at least one of all types of information capable of identifying the object, for example, a name, a resident registration number, a birth date, a personal ID number, a personal ID code, and biometric information (e.g., a face, an iris, and a fingerprint).

In operation S120, first body information of the object is obtained based on the ID information of the object input via the input interface 370. According to an embodiment, the controller 320 may obtain first body information of the object corresponding to ID information of the object stored in the storage 350 or an external device, by using the ID information of the object input via the input interface 370. At this time, the storage 350 included in the diagnosis part 30 or an external device communicable with the diagnosis part 30 via the communication interface 360 may store the first body information of the object. The first body information of the object means all pieces of pre-storable body information of the object necessary for an obstetric and gynecologic treatment, for example, a gestation period of a mother who is carrying a fetus, the number of fetuses, the location of a fetus, the weight of the mother, the height of the mother, the body temperature of the mother, the examination history of the mother, and the medical history of the mother.

In operation S140, a control signal for the chair unit 400 is generated based on the obtained first body information of the object. According to an embodiment, the controller 320 may ascertain a diagnosis state and body information of the object by using the obtained first body information of the object. At this time, the chair unit 400 may be changed according to the diagnosis state and the body information of the object, and the controller 320 may generate a control signal capable of generating a driving force for transforming the chair unit 400.

In operation S150, based on the control signal generated by the controller 320, the chair unit 400 is changed from an initial state to a diagnosis state. According to an embodiment, based on the control signal generated by the controller 320, the driver 50 may generate a driving force and change the chair unit 400 from the initial state to the diagnosis state. For example, the chair unit 400 may be changed from the initial state to the first through third diagnosis states, according to the body information of the object, for example, a gestation period. At this time, a visual indicator or an auditory indicator as the indicator 380 may make the object know that the change of the chair unit 400 from an initial state to a diagnosis state.

According to an embodiment, in the initial state, the chair unit 400 may be a structure in which it is easy for the object to sit on the chair unit 400, as shown in FIGS. 7A to 7C. For example, in the initial state, the upper body support 420 may be arranged to have a first angle α of 90° to 120° counter-clockwise with respect to the seat 410. At this time, the leg cradle 430 may be arranged to have a second angle β of 240° to 360° clockwise with respect to the seat 410. The ultrasound probe 20 and the diagnosis part 30 may be arranged adjacent to the seat 410 such that the object is not interfered while sitting down on the chair unit 400.

According to an embodiment, when the object, namely, a pregnant woman, is in an early stage (10 weeks or less of pregnancy) as shown in FIGS. 8A to 8C, the first diagnosis state may be a structure of the chair unit 400 for diagnosing a lower body part of the object. For example, in the first diagnosis state, the upper body support 420 may be inclined to have a flat state, namely, a first angle α of 180°, with respect to the seat 410. However, embodiments of the present disclosure are not limited thereto, and, as necessary, the upper body support 420 may be inclined at a first angle α, for example, an angle of 110° to 180°, with respect to the seat 410, during a diagnosis. The leg cradle 430 may also be inclined to have a second angle β of 120° to 180° clockwise with respect to the seat 410. The seat 410 may also be inclined to have an angle of 0° to 20° with respect to the ground. At this time, the first cradle 431 and the second cradle 432 included in the leg cradle 430 may be moved such that one of the first cradle 431 is spaced apart from one end of the second cradle 432, and the secretion container 450 may be arranged between the first cradle 431 and the second cradle 432.

At this time, the chair unit 400 may be arranged to ascend or descend from the ground according to the height of the user and a diagnosis type. For example, the ultrasound probe 20 and the diagnosis part 30 may also be arranged to ascend or descend from the ground according to the height of the user and the diagnosis type, and may be arranged more adjacent to the leg cradle 430 than to the seat 410 considering the arm length of the user and the diagnosis type, thereby maximizing the usage convenience of the user.

According to an embodiment, when the object, namely, a pregnant woman, is in a middle stage (10 to 30 weeks of pregnancy) as shown in FIGS. 9A and 9B, the second diagnosis state may be in a structure of the chair unit 400 for diagnosing an abdomen part of the object. For example, in the second diagnosis state, the seat 410, the upper body support 420, and the leg cradle 430 may be arranged on a plane. In other words, the upper body support 420 may be inclined to have a flat state, namely, a first angle α of 180°, with respect to the seat 410. However, embodiments of the present disclosure are not limited thereto, and, as necessary, the upper body support 420 may be inclined at a first angle α, for example, an angle of 110° to 180°, with respect to the seat 410, during a diagnosis. Mattes related to the ascending and descending of the chair unit 400 and the movements of the ultrasound probe 20 and the diagnosis part 30 according to the height of the user and the diagnosis type are substantially the same as those in the first diagnosis state, and thus descriptions thereof will be omitted.

According to an embodiment, when the object, namely, a pregnant woman, is in a late stage (30 weeks or more of pregnancy) as shown in FIGS. 10A to 10C, the third diagnosis state may be a structure of the chair unit 400 for diagnosing an abdomen part of the object. When the state of a pregnant woman is in the later stages of pregnancy, it is hard for the pregnant woman to lie flat on her back due to the weight of the fetus. Accordingly, considering the diagnosis convenience of the object, the upper body support 420 needs to move relative to the seat 410. For example, in the third diagnosis state, the upper body support 420 may be inclined to have a first angle α of 110° to 170° counter-clockwise with respect to the seat 410. The leg cradle 430 may be arranged on the same plane as the seat 410. Mattes related to the ascending and descending of the chair unit 400 and the movements of the ultrasound probe 20 and the diagnosis part 30 according to the height of the user and the diagnosis type are substantially the same as those in the first diagnosis state, and thus descriptions thereof will be omitted.

Referring back to FIG. 6, in operation S170, when the diagnosis of the object by the user is completed, diagnosis completion information is input. According to an embodiment, when the diagnosis of the object by the user is completed, the user may hold the probe 210 on the probe holder 230 as shown in FIG. 5A. When the probe sensor 231 senses that the probe 210 is held on the probe holder 230 for a certain period of time, it may be recognized that the diagnosis of the object has been completed, and, diagnosis completion information indicating that the diagnosis of the object has been completed may be input. However, embodiments of the present disclosure are not limited thereto, and the diagnosis completion information may be directly input by the user by using the input interface 370.

In operation S180, when the diagnosis completion information is input, the chair unit 400 is transformed from the diagnosis state to the initial state, based on the control signal generated by the controller 320. According to an embodiment, based on the control signal generated by the controller 320, the driver 50 may generate a driving force and transform the chair unit 400 from the diagnosis state to the initial state. At this time, a visual indicator or an auditory indicator as the indicator 380 may make the object know the completion of the diagnosis of the object and the transformation of the chair unit 400 from the diagnosis state to the initial state.

Figure 11:
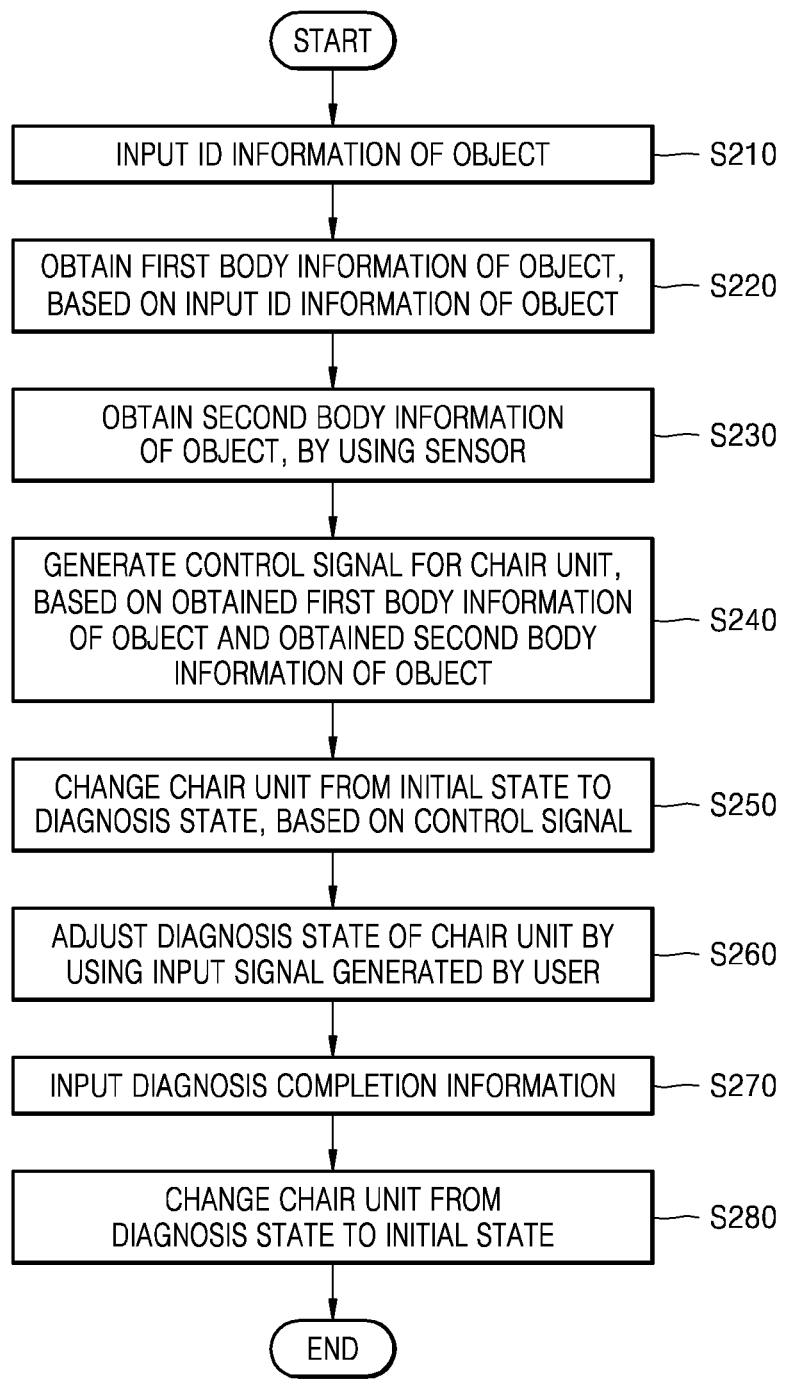
FIG. 11 is a flowchart of an obstetric and gynecologic diagnosis method according to another embodiment.

FIG. 11 is a flowchart of an obstetric and gynecologic diagnosis method according to another embodiment. Operations other than operations S230, S240, and S260 of the obstetric and gynecologic diagnosis method of FIG. 11 are substantially the same as those of FIG. 6. Thus, for convenience of explanation, operations S230, S240, and S260 of FIG. 11 different from FIG. 6 will be focused.

Referring to FIG. 11, in operation S230, second body information of the object is obtained by the sensor 41. According to an embodiment, the sensor 41 may sense body information of the object, for example, a current weight, a body temperature, or a sudden seating state change of the object occurring during a diagnosis of the object, from the object seated on the chair unit 400, and may transmit measured body information of the object and location movement information of the object to the controller 320. When the object is a mother who is carrying a fetus, a sharp weight change and a sharp body temperature change may occur according to a growth of the fetus. A sudden seating state change of the object may also occur during a diagnosis of the object. The second body information of the object is obtained by sensing such a real-time change and may be different from the first body information of the object pre-stored in the storage 350.

In operation S240, a control signal for the chair unit 400 is generated based on the obtained first and second body information of the object. According to an embodiment, the controller 320 may ascertain a diagnosis state and body information of the object by using the first body information of the object obtained using information stored in the storage 350 and the second body information of the object obtained in real time by using the sensor 41. At this time, the chair unit 400 may be changed according to the diagnosis state and the body information of the object, and the controller 320 may generate a control signal capable of generating a driving force for transforming the chair unit 400.

In operation S260, the diagnosis state of the chair unit 400 is adjusted using an input signal generated by the user. According to an embodiment, as described above, based on the control signal generated by the controller 320, the driver 50 may generate a driving force and change the chair unit 400 from the initial state to the diagnosis state. However, the change of the chair unit 400 to the diagnosis state based on the first body information and the second body information of the object may not completely coincide with a diagnosis environment. At this time, the user may input to the input interface 370 an input signal for transforming the chair unit 400. The input signal may be transmitted to the controller 320, and, based on the control signal generated by the controller 320,6 the driver 50 may generate a driving force and adjust the diagnosis state of the chair unit 400 such that the diagnosis state of the chair unit 400 coincides with a current diagnosis environment.

As described above, the diagnosis state of the chair unit 400 may be adjusted in three stages by using the first body information of the object pre-stored in the storage 350, using the second body information of the object obtained in real time by the sensor 41, and using the input signal generated by the user, and thus diagnosis convenience of the object may be secured. However, embodiments of the present disclosure are not limited thereto, and the adjustment of the diagnosis state of the chair unit 400 in a stage of using the second body information of the object or using the input signal generated by the user from among the three stages may be omitted according to a diagnosis environment and an adjustment necessity.

Figure 12:
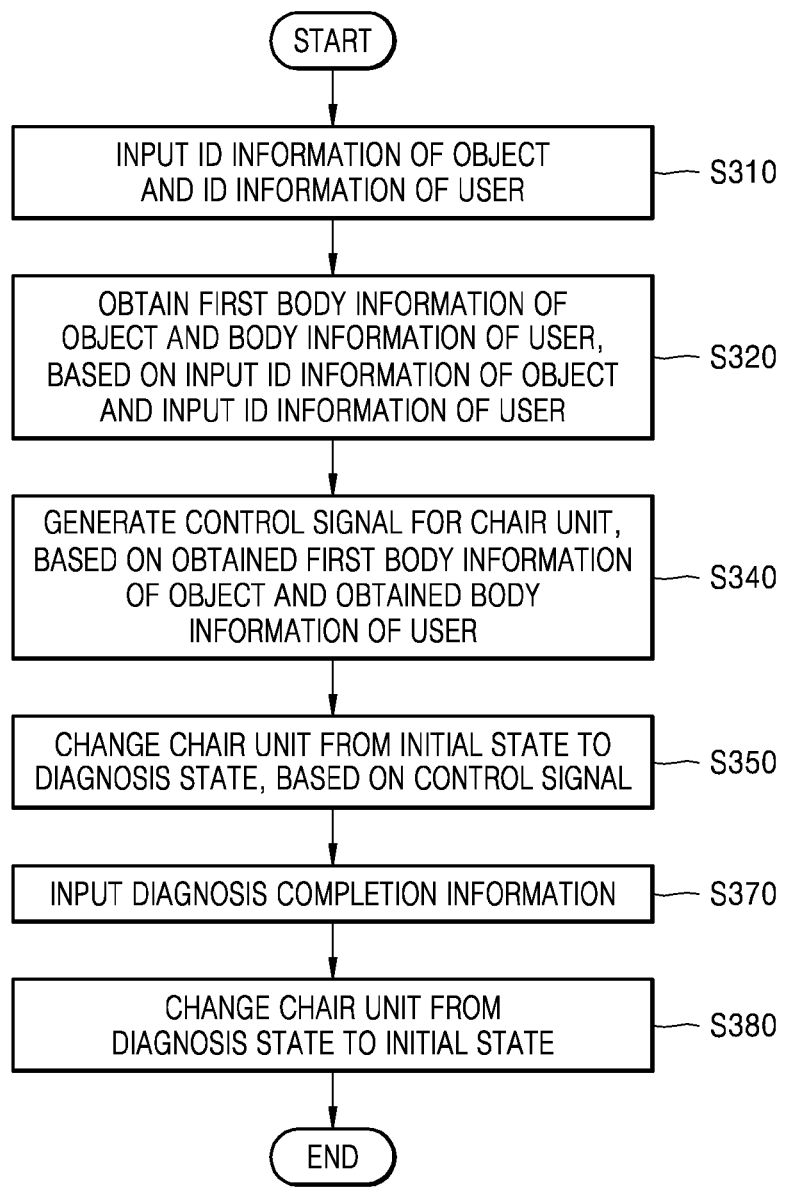
FIG. 12 is a flowchart of an obstetric and gynecologic diagnosis method according to another embodiment.

FIG. 12 is a flowchart of an obstetric and gynecologic diagnosis method according to another embodiment. Operations other than operations S310, S320, and S340 of the obstetric and gynecologic diagnosis method of FIG. 12 are substantially the same as those of FIG. 6. Thus, for convenience of explanation, operations S310, S320, and S340 of FIG. 12 different from FIG. 6 will be focused.

Referring to FIG. 12, in operation S310, the ID information of the object and the ID information of the user are input via the input interface 370 included in the diagnosis part 30. For example, the ID information of the object and the ID information of the user means at least one of all types of information capable of identifying the object and the user, for example, a name, a resident registration number, a birth date, a personal ID number, a personal ID code, and biometric information (e.g., a face, an iris, and a fingerprint).

In operation S320, first body information of the object and body information of the user are obtained based on the ID information of the object and the ID information of the user input via the input interface 370. According to an embodiment, the controller 320 may obtain first body information of the object corresponding to ID information of the object stored in the storage 350 or an external device and body information of the user corresponding to the ID information of the user, by using the ID information of the object and the ID information of the user input via the input interface 370. At this time, the storage 350 included in the diagnosis part 30 or an external device communicable with the diagnosis part 30 via the communication interface 360 may store the first body information of the object and the body information of the user. The first body information of the object means all pieces of pre-storable body information of the object necessary for an obstetric and gynecologic treatment, for example, a gestation period of a mother who is carrying a fetus, the number of fetuses, the location of a fetus, the weight of the mother, the height of the mother, the body temperature of the mother, the examination history of the mother, and the medical history of the mother. The body information of the user means all pieces of body information of the user necessary to perform an obstetric and gynecologic treatment by manipulating the probe 210, for example, a surgical procedure posture of the user, the arm length of a surgical operator, an eye position of the surgical operator, the height thereof, the sitting height thereof, and the length of the arms thereof.

In operation S340, a control signal for the chair unit 400 is generated based on the obtained first body information of the object and the body information of the user. According to an embodiment, the controller 320 may ascertain a diagnosis state and body information of the object and the body information of the user by using the first body information of the object obtained using information stored in the storage 350 and the ID information of the user. At this time, the chair unit 400 may be changed according to the diagnosis state and the body information of the object and the body information of the user, and the controller 320 may generate a control signal capable of generating a driving force for transforming the chair unit 400.

In operation S350, based on the control signal generated by the controller 320, the chair unit 400 is changed from an initial state to a diagnosis state. According to an embodiment, based on the control signal generated by the controller 320, the driver 50 may generate a driving force and change the chair unit 400 from the initial state to the diagnosis state. For example, the chair unit 400 may be changed from the initial state to the first through third diagnosis states, according to the body information of the object, for example, a gestation period. At this time, a visual indicator or an auditory indicator as the indicator 380 may make the object know that the change of the chair unit 400 from an initial state to a diagnosis state. At this time, the chair unit 400 may be arranged to ascend or descend from the ground according to the body information of the user, for example, the height and sitting height of the user, as shown in FIGS. 8A to 10B. For example, the ultrasound probe 20 and the diagnosis part 30 may also be arranged to ascend or descend from the ground according to the height, sitting height, and arm length of the user, a diagnosis type, and a diagnosis posture, and may be arranged more adjacent to the leg cradle 430 than to the seat 410 considering the arm length of the user and the diagnosis type, thereby maximizing the usage convenience of the user.

An obstetric and gynecologic diagnosis apparatus according to an embodiment is automatically transformed according to body information of a pregnant woman and obstetric and gynecologic information thereof, thereby improving convenience of the pregnant woman or the user and minimizing a diagnosis period of time and shame and anxiety of the pregnant woman.

While an obstetric and gynecologic diagnosis apparatus and an obstetric and gynecologic diagnosis method using the same have been particularly shown and described with reference to exemplary embodiments thereof, it will be understood by those of ordinary skill in the art that various changes in form and details may be made therein without departing from the spirit and scope as defined by the following claims.

What is claimed is:

1. An obstetric and gynecologic diagnosis apparatus comprising:
    a chair unit comprising an upper body support, a set, and a leg cradle sequentially arranged in one direction and connected to each other,
    a controller configured to generate a control signal for moving at least one of the upper body support, the seat, or the leg cradle according to first body information of an object including a gestation period of the object; and
    a driver configured to generate a driving force for moving at least one of the upper body support, the seat, or the leg cradle according to the control signal,
    wherein relative position of the upper body support, the seat, and the leg cradle is changed according to a change of the gestation period of the object.

2. The obstetric and gynecologic diagnosis apparatus of claim 1, further comprising:
    a storage configured to store the first body information of the object; and
    an input interface configured to input identification (ID) information of the object,
    wherein the first body information of the object is identified by the ID information of the object, and the ID information of the object is at least one of name information of the object, fingerprint information of the object, face information of the object, an ID code corresponding to the object.

3. The obstetric and gynecologic diagnosis apparatus of claim 2, wherein user ID information comprising body information of a user is input to the input interface, and the controller generates the control signal for moving at least one of the upper body support, the seat, or the leg cradle according to the first body information of the object and the body information of the user.

4. The obstetric and gynecologic diagnosis apparatus of claim 1, further comprising at least one ultrasound probe configured to transmit an ultrasound signal to the object and receive an ultrasound echo signal from the object, the at least one ultrasound probe being connected to the chair unit to be movable with respect to the chair unit.

5. The obstetric and gynecologic diagnosis apparatus of claim 4, further comprising a diagnosis part comprising the controller, an input interface, and a display that displays a diagnosis image of the object, the diagnosis part being connected to the chair unit to be movable with respect to the chair unit.

6. The obstetric and gynecologic diagnosis apparatus of claim 1, wherein the chair unit is arranged to be vertically movable with respect to a ground, the upper body support is connected to the seat to be rotatable about one axis, and the leg cradle is connected to the seat to be rotatable about the axis.

7. The obstetric and gynecologic diagnosis apparatus of claim 6, wherein, in a first diagnosis state, the upper body support is arranged on a same plane as the seat, and the leg cradle is inclined at an angle of 120° to 180° clockwise with respect to the seat.

8. The obstetric and gynecologic diagnosis apparatus of claim 6, wherein, in a second diagnosis state, the upper body support, the seat, and the leg cradle are arranged on one plane.

9. The obstetric and gynecologic diagnosis apparatus of claim 8, wherein the leg cradle comprises a first cradle and a second cradle on which both legs of the object are respectively placed, and the first cradle and the second cradle are arranged such that one end of the first cradle is spaced apart from one end of the second cradle.

10. The obstetric and gynecologic diagnosis apparatus of claim 6, wherein, in a third diagnosis state, the upper body support is inclined at an angle of 110° to 170° counterclockwise with respect to the seat, and the leg cradle is arranged on a same plane as the seat.

11. The obstetric and gynecologic diagnosis apparatus of claim 4, further comprising:
    a probe holder configured to hold the at least one ultrasound probe; and a probe sensor configured to sense whether the at least one ultrasound probe has been held on the probe holder.

12. The obstetric and gynecologic diagnosis apparatus of claim 1, further comprising at least one sensor configured to sense second body information of the object,
wherein the controller generates the control signal for moving at least one of the upper body support, the seat, or the leg cradle according to the first body information of the object and the second body information of the object.

13. An obstetric and gynecologic diagnosis method comprising:
obtaining first body information of an object including a gestation period of the object;
generating a control signal for a chair unit comprising an upper body support, a seat, and a leg rest, based on a change of the gestation period of the object;
changing relative position of the upper body support, the seat, and the leg rest according to the control signal;
inputting diagnosis completion information; and
changing relative position of the upper body support, the seat, and the leg rest to an initial state.

14. The obstetric and gynecologic diagnosis method of claim 13, further comprising inputting identification (ID) information of the object,
wherein the first body information of the object is obtained based on the ID information of the object, and the ID information of the object is at least one of name information of the object, fingerprint information of the object, face information of the object, or an ID code corresponding to the object.

15. The obstetric and gynecologic diagnosis method of claim 13, wherein
the changing relative position of the upper body support, the seat, and the leg rest comprises changing to a diagnosis state;
the diagnosis state is one of first through third diagnosis states, wherein,
in the first diagnosis state, the upper body support is arranged on a same plane as the seat, and the leg cradle is inclined at an angle of 120° to 180° clockwise with respect to the seat,
in the second diagnosis state, the upper body support, the seat, and the leg cradle are arranged on one plane, and
in the third diagnosis state, the upper body support is inclined at an angle of 110° to 170° counterclockwise with respect to the seat, and the leg cradle is arranged on a same plane as the seat.

16. The obstetric and gynecologic diagnosis method of claim 13, wherein, when a probe has been held on a probe holder for a certain period of time or mom, the diagnosis completion information is inputted.

17. The obstetric and gynecologic diagnosis method of claim 13, further comprising obtaining second body information of the object by using a sensor,
wherein the second body information of the object is at least one of a weight, a body temperature, a sitting state, or a sitting duration time.

18. The obstetric and gynecologic diagnosis method of claim 17, wherein the control signal for the chair unit is generated based on the obtained first body information of the object and the obtained second body information of the object.

19. The obstetric and gynecologic diagnosis method of claim 18, further comprising adjusting a diagnosis state of the chair unit by using an input signal generated by a user.

20. An obstetric and gynecologic diagnosis method comprising:
obtaining first body information of an object including a gestation period of the object and body information of a user;
generating a control signal for a chair unit comprising upper a body support, a seat, and a leg rest, based on a change of the gestation period of the object and the obtained body information of the user;
changing relative position of the upper body support, the seat, and the leg rest according to the control signal;
inputting diagnosis completion information; and
changing relative of the upper body support, the seat, and the leg rest to an initial state.

\* \* \* \* \*